(12) United States Patent
Tanaka et al.

(10) Patent No.: US 9,617,298 B2
(45) Date of Patent: Apr. 11, 2017

(54) COLLAGEN POWDER AND/OR COLLAGEN-DERIVED POWDER, AND PRODUCTION METHOD FOR THE SAME

(75) Inventors: Keisuke Tanaka, Tokyo (JP); Takayuki Ogura, Tokyo (JP); Shunji Hattori, Tokyo (JP); Koichi Matsuda, Tokyo (JP); Yoshikatsu Kobayashi, Tokyo (JP); Shoji Oi, Tokyo (JP)

(73) Assignee: NIPPI, INCORPORATED, Tokyo (JP)

( * ) Notice: Subject to any disclaimer, the term of this patent is extended or adjusted under 35 U.S.C. 154(b) by 455 days.

(21) Appl. No.: 13/813,126

(22) PCT Filed: Jul. 29, 2011

(86) PCT No.: PCT/JP2011/067556
§ 371 (c)(1),
(2), (4) Date: Apr. 5, 2013

(87) PCT Pub. No.: WO2012/015055
PCT Pub. Date: Feb. 2, 2012

(65) Prior Publication Data
US 2013/0190479 A1     Jul. 25, 2013

(30) Foreign Application Priority Data

Jul. 30, 2010  (JP) ................................. 2010-172698
Jul. 30, 2010  (JP) ................................. 2010-172699

(51) Int. Cl.
| | |
|---|---|
| C07K 1/30 | (2006.01) |
| A61K 9/14 | (2006.01) |
| A61K 8/02 | (2006.01) |
| A61K 8/65 | (2006.01) |
| C08J 3/14 | (2006.01) |
| C08L 89/06 | (2006.01) |
| A61Q 19/00 | (2006.01) |
| C08H 1/06 | (2006.01) |

(52) U.S. Cl.
CPC .............. C07K 1/30 (2013.01); A61K 8/022 (2013.01); A61K 8/65 (2013.01); A61Q 19/00 (2013.01); C08H 1/06 (2013.01); C08J 3/14 (2013.01); C08L 89/06 (2013.01); *A61K 2800/10* (2013.01); *C08J 2389/06* (2013.01)

(58) Field of Classification Search
CPC .......... C07K 1/30; C07K 1/303; A61K 8/022; A61K 8/65; C08J 3/14; C08L 89/06; A61Q 19/00; C08H 1/06
See application file for complete search history.

(56) References Cited

U.S. PATENT DOCUMENTS

| | | | |
|---|---|---|---|
| 3,637,642 A | | 1/1972 | Fujii |
| 4,215,200 A | * | 7/1980 | Miyata ................... C07K 14/78 106/150.1 |
| 4,412,947 A | * | 11/1983 | Cioca ....................... A61K 9/70 106/150.1 |
| 4,837,285 A | * | 6/1989 | Berg ........................ A61K 9/70 128/DIG. 8 |
| 5,274,078 A | | 12/1993 | Wada et al. |
| 5,412,076 A | * | 5/1995 | Gagnieu ............... A61L 15/325 106/150.3 |
| 2002/0150598 A1 | | 10/2002 | Hamada et al. |
| 2009/0226557 A1 | | 9/2009 | Etayo Garralda et al. |

FOREIGN PATENT DOCUMENTS

| | | |
|---|---|---|
| JP | 44-1175 | 1/1969 |
| JP | 46-15033 | 4/1971 |
| JP | 58-52662 B2 | 11/1983 |
| JP | 64-11132 A | 1/1989 |
| JP | 4-226538 A | 8/1992 |
| JP | 6-228505 A | 8/1994 |
| JP | 8-27035 A | 1/1996 |
| JP | 8-27192 A | 1/1996 |
| JP | 2000-128764 A | 5/2000 |
| JP | 2000-256398 A | 9/2000 |
| JP | 2005-325056 A | 11/2005 |
| JP | 2005-343853 A | 12/2005 |
| JP | 2008-266222 A | 11/2008 |
| JP | 2009-102311 A | 5/2009 |
| JP | 2009-529591 A | 8/2009 |

OTHER PUBLICATIONS

Sigma-Aldrich Particle Size Conversion Table: 2 pages total; retrieved from the internet Dec. 3, 2015.*
Usha, R., et al. 2006 Colloids and Surfaces B: Biointerfaces 48: 101-105.*
International Search Report issued in PCT/JP2011/067556 mailed Aug. 30, 2011.
Japanese Office Action and partial English tranlation issued Mar. 24, 2015 for JP Application No. 2011-167822.
Extended European Search Report issued Dec. 4, 2013, in European Patent Application No. 11812644.0.

* cited by examiner

*Primary Examiner* — Marsha Tsay
(74) *Attorney, Agent, or Firm* — Birch, Stewart, Kolasch & Birch, LLP

(57) ABSTRACT

Disclosed is a collagen powder and/or a collagen derivative powder, which are obtained by dispersing in a hydrophilic organic solvent a crude collagen precipitate which comprises 12 to 50% by mass of a collagen precipitate and/or a collagen derivative precipitate having an average particle size of 1 to 1,000 μm, recovering solids and then drying the solids. By dispersing the crude collagen precipitate in the hydrophilic organic solvent, the resulting precipitates can be dehydrated, so that drying of the thus obtained solids can be done by air-drying. In addition, the resulting collagen powder and/or collagen derivative powder exhibit excellent solubility due to an increased specific surface area and also have excellent ease of handling with the average particle size being 8 to 1,000 μm.

25 Claims, 7 Drawing Sheets

COLLAGEN POWDER AND/OR COLLAGEN-DERIVED POWDER, AND PRODUCTION METHOD FOR THE SAME

TECHNICAL FIELD

The present invention relates to a collagen powder and/or a collagen derivative powder, which are obtained by dispersing a crude collagen precipitate in a hydrophilic organic solvent and drying the resulting dispersion, the crude collagen precipitate comprising a collagen precipitate and/or a collagen derivative precipitate and having an average particle size of 1 to 1,000 μm; and a method of producing the same.

BACKGROUND ART

Collagen has a triple-helical structure in which three polypeptide strands are wound around each other and a plurality of collagen molecules of about 300 nm in length are associated and staggered from each other by 67 nm to form a long collagen fiber. Collagen is a principal protein which constitutes skins, tendons, bones and the like of, for example, fish, pigs and cattle, and the majority of collagen is found in the form of insoluble fiber in vivo.

Although collagen fiber is insoluble, it has advantages, for example, in that it is a biological component and thus highly safe and that, because of the high homology among animals, it is not likely to cause an immunoreaction. Therefore, application of collagen has been investigated in the fields of food products, medicines and cosmetics, and there have been developed a variety of solubilization methods and application methods for solubilized collagen. Examples of solubilized collagen include, in addition to those obtained by extracting a trace amount of a soluble collagen contained in a material such as an animal skin or bone with a dilute acid, collagen solubilized by an addition of an enzyme such as protease (Patent Literature 1) and collagen solubilized by an addition of an alkali (Patent Literature 2).

Meanwhile, since water-soluble collagen has a low thermal denaturation temperature when it is in a solubilized state having a large water content and being transparent, there is also disclosed collagen having an improved thermal denaturation temperature (Patent Literature 3). Water-insoluble associations of collagen having an isoelectric point in the pH range of cosmetic formulations had been considered unsuitable as cosmetic materials due to several reasons such as their opaque white color and heterogeneity; however, in Patent Literature 3, it was discovered that a collagen association obtained by adjusting an aqueous solution of collagen having an isoelectric point at a pH of 5.5 to 8.5 to have a pH in the vicinity of the isoelectric point has a notably high thermal denaturation temperature and such association was used as a cosmetic material. In Examples of Patent Literature 3, a collagen solution having an isoelectric point at about pH 7.0 was salt-precipitated by adding thereto sodium chloride to a final concentration of 5% by mass. The thus obtained collagen precipitates were dissolved with hydrochloric acid and the resulting solution was then neutralized with sodium hydroxide to yield a dispersion of collagen associations. An undenatured collagen molecule is rod-shaped and has a unique triple-helix structure; however, since an aqueous collagen solution thereof has a low heat resistance, the helical structure of the collagen molecule is easily disrupted by a heat treatment. In the above-described Patent Literature 3, using undenatured collagen molecules that were obtained, the adhesion thereto of human epidermal cell was evaluated. It was shown that, in the case of gelatin, the human epidermal cell did not at all exhibit adhesion after 30 minutes of culturing and a very slight adhesion was observed after 3 hours of culturing; however, in the cases where undenatured collagen molecules were used, notable adhesion was observed after 30 minutes of culturing.

An undenatured collagen solution may be denatured even at normal temperature; therefore, storage thereof requires temperature control by refrigeration or the like. In view of such storage stability of collagen, there is disclosed a method of using a dry collagen (Patent Literature 4). In this method, a collagen solution is injected via a nozzle into a volatile hydrophilic organic solvent medium to yield a fibrous or membranous product and the thus obtained fibrous product or the like is then dried and shredded or pulverized to produce a granular or powdery collagen dry product. It is described that the collagen solution to be injected into the hydrophilic organic solvent medium preferably has a collagen concentration of 3 to 10% by mass and that the injection rate from the nozzle is preferably 1 to 30 m/min.

Furthermore, there is also disclosed a dried product of a collagen derivative originated from fish skin (Patent Literature 5). The invention of Patent Literature 5 is characterized in that a treatment with an organic solvent and a centrifugation treatment are performed in combination in order to reduce the odor of fish-originated collagen and that a collagen derivative such as an acylated collagen is prepared as collagen. In Example 2, after subjecting fish skin to an organic solvent treatment and a centrifugation treatment, the resulting collagen was solubilized with acetic acid and salt precipitation was performed to yield collagen precipitates, which were then freeze-dried to obtain dry collagen. Further, in Example 4, after subjecting fish skin to an organic solvent treatment and a centrifugation treatment and adding sodium hydroxide to the resulting precipitates, the resulting solution was stirred overnight and then centrifuged. Thereafter, an aqueous citric acid solution was added to the precipitates to extract collagen, which was then precipitated with an addition of sodium citrate, and the solution was adjusted to have a pH of 10 by adding a sodium hydroxide solution to the thus obtained collagen precipitates. Then, succinic anhydride was allowed to react with the collagen precipitates to obtain a succinylated collagen, which was subsequently precipitated with hydrochloric acid. Finally, the resulting precipitates were freeze-dried to obtain dry collagen product.

Moreover, collagen has different isoelectric point depending on the treatment method and a collagen solubilized under acidic conditions has an isoelectric point at a pH of 7 to 9.5; therefore, such a collagen has poor solubility at a pH of 5 or higher and forms precipitates and aggregates. In view of this point, there is also disclosed a method in which the water-solubility of collagen is improved by esterification (Patent Literature 6). In Patent Literature 6, an esterification reaction of collagen is performed in advance in an animal tissue condition and then extraction operations of the thus esterified collagen are performed. It is described that an esterified collagen can be thereby produced inexpensively with simple steps.

PRIOR ART LITERATURE

Patent Literature

Patent Literature 1: Examined Japanese Patent Application Kokoku Publication No. S44-1175
Patent Literature 2: Examined Japanese Patent Application Kokoku Publication No. S46-15033

Patent Literature 3: Unexamined Japanese Patent Application Kokai Publication No. 2000-128764

Patent Literature 4: Unexamined Japanese Patent Application Kokai Publication No. H6-228505

Patent Literature 5: Unexamined Japanese Patent Application Kokai Publication No. 2000-256398

Patent Literature 6: Unexamined Japanese Patent Application Kokai Publication No. H8-27192

DISCLOSURE OF THE INVENTION

Problem to be Solved by the Invention

Undenatured collagen retaining a triple-helix structure has excellent moisture-retaining properties as well as excellent adhesion to human epidermal cells; therefore, it is a compound for which formulation into cosmetics and medical applications are demanded to be developed. However, since collagen dissolved in a solution has a low thermal denaturation temperature and is thus denatured even at normal temperature, refrigeration is required for storage. In other words, collagen cosmetics in which a collagen retaining a triple-helix structure is formulated in a dissolved state are required to be stored in a refrigerator or the like in order to prevent denaturation of the collagen; therefore, the use of such collagen cosmetics is not simple. In addition, since collagen easily precipitates at its isoelectric point, when the pH of a collagen solution is shifted due to bacterial contamination or the like, the solution becomes cloudy, or clogging or the like may be caused by precipitation. Therefore, there is a demand for a method of producing undenatured collagen powder which is capable of constituting a triple-helix structure in a dissolved state.

Meanwhile, since collagen is swollen with only a small amount of water, the production of collagen powder is not easy. In the method disclosed in the above-described Patent Literature 4, in order to obtain dry collagen, a solubilized collagen solution is injected into an organic solvent to form a thread; however, the operations in the thread formation are extremely complicated. In addition, in Patent Literature 5, a dry collagen is obtained by freeze-drying a collagen; however, the treatment time is long and the energy required for the drying is enormous.

Collagen is a compound which intrinsically has excellent moisture-retaining properties. In Comparative Example 1 of the above-described Patent Literature 6, it is described that, although an attempt was made to perform ethanol washing on collagen precipitates obtained by salt precipitation of an atelocollagen, since the collagen aggregates included sodium chloride-containing water, the water could not be removed. As in this case, the drying of collagen requires technologies such as freeze-drying and spray-drying and this makes the production processes and apparatuses complex. Therefore, there is a demand for a simple preparation method of a collagen powder which does not require complex processes.

Meanwhile, as shown in the above-described Patent Literature 3, undenatured collagen has activities such as excellent adhesion during cell culture. Thus, even in the case of a collagen powder, the collagen powder is required to maintain its triple-helix structure when dissolved. For example, there is a method in which a solution containing a component of interest is supplied to the column top via a pressure nozzle and hot air is blown therein to perform granulation. However, since collagen is easily denatured by heat, it is also difficult to perform granulation of collagen by such a method. Therefore, there is a demand for a method of producing undenatured collagen powder capable of constituting a triple-helix structure in a dissolved state, in which method the production processes are simple and the production energy is low.

Furthermore, in the first place, a soluble collagen has an isoelectric point which is dependent on the extraction method and the solubility of a soluble collagen is low at its isoelectric point. Therefore, it is difficult to dissolve a dry collagen by using a neutral cosmetic liquid or the like. Accordingly, in cases where a soluble collagen is used in a cosmetic application, a collagen powder capable of readily dissolving at a pH of ordinary cosmetics, which is 5.5 to 8.5, is desired.

Powderization of collagen is similarly demanded not only for native collagens, but also for collagen derivatives.

In view of the above-described circumstances, an objective of the present invention is to provide a fine collagen powder and/or collagen derivative powder.

Further, another objective of the present invention is to provide a production method by which undenatured collagen powder and/or collagen derivative powder can be easily prepared.

Means for Solving the Problem

The present inventors discovered that, when a collagen solution is isoelectrically precipitated, collagen associates with each other to precipitate in the solution; however, when a collagen solution is isoelectrically precipitated with stirring, a crude collagen precipitate composed of a collagen precipitates having an average particle size of 1 to 1,000 μm, which is smaller than that of conventional collagen aggregate, can be obtained; that, when the above-described crude collagen precipitate is adjusted to have a concentration of 12 to 50% by mass and dispersed in a hydrophilic organic solvent, solids can be efficiently recovered by dehydrating the resulting collagen precipitates and a collagen powder is obtained by air-drying the solids; that, by using a crude collagen precipitate having a small particle size, dehydration and drying can be efficiently performed and consequently, a collagen powder having a small particle size can be produced; that a collagen powder obtained by the above-described method is not denatured even at a high temperature of 110° C. and has excellent heat resistance; and that, when this powder is dissolved, the collagen retains a triple-helix structure in the resulting solution, thereby completing the present invention.

That is, the present invention provides a collagen powder and/or a collagen derivative powder, which are obtained by dispersing in a hydrophilic organic solvent a crude collagen precipitate which comprises 12 to 50% by mass of a collagen precipitate and/or a collagen derivative precipitate having an average particle size of 1 to 1,000 μm, recovering solids and then drying the thus recovered solids.

The present invention also provides a method of producing a collagen powder and/or a collagen derivative powder, which is characterized by comprising the steps of: obtaining isoelectric precipitates having an average particle size of 1 to 1,000 μm by isoelectrically precipitating a solution containing a collagen and/or a collagen derivative at a pH of 3.5 to 10 while controlling association of the collagen and/or the collagen derivative; adjusting the concentration of the resulting collagen precipitate and/or collagen derivative precipitate contained in the above-described isoelectric precipitates to prepare a crude collagen precipitate containing 12 to 50% by mass of the collagen precipitate and/or the collagen derivative precipitate; dispersing the thus obtained crude collagen precipitate in a hydrophilic organic solvent; recovering solids; and drying the thus recovered solids.

Further, the present invention provides a method of producing a collagen powder and/or a collagen derivative powder, which is characterized by comprising the steps of: obtaining isoelectric precipitates having an average particle size of 1 to 1,000 μm by isoelectrically precipitating a solution containing a collagen and/or a collagen derivative at a pH of 3.5 to 10 and then pulverizing the resulting precipitates into particles; adjusting the concentration of the resulting collagen precipitate and/or collagen derivative precipitate contained in the above-described isoelectric precipitates to prepare a crude collagen precipitate containing 12 to 50% by mass of the collagen precipitate and/or the collagen derivative precipitate; dispersing the thus obtained crude collagen precipitate in a hydrophilic organic solvent; recovering solids; and drying the thus recovered solids.

Still further, the present invention provides a method of producing a collagen powder and/or a collagen derivative powder, which is characterized by comprising the steps of obtaining salt precipitates having an average particle size of 1 to 1,000 μm by subjecting a solution containing a collagen and/or a collagen derivative to salt precipitation while controlling association of the collagen and/or the collagen derivative; adjusting the concentration of the resulting collagen precipitate and/or collagen derivative precipitate contained in the above-described salt precipitates to 12 to 50% by mass, thereby preparing a crude collagen precipitate; dispersing the thus obtained crude collagen precipitate in a hydrophilic organic solvent; recovering solids; and drying the thus recovered solids.

Yet still further, the present invention provides a method of producing a collagen powder and/or a collagen derivative powder, which is characterized by comprising the steps of: obtaining salt precipitates having an average particle size of 1 to 1,000 μm by subjecting a solution containing a collagen and/or a collagen derivative to salt precipitation and then pulverizing the resulting salt precipitates into particles; adjusting the concentration of the resulting collagen precipitate and/or collagen derivative precipitate contained in the above-described salt precipitates to 12 to 50% by mass, thereby preparing a crude collagen precipitate; dispersing the thus obtained crude collagen precipitate in a hydrophilic organic solvent; recovering solids; and drying the thus recovered solids.

Yet still further, the present invention provides the above-described method of producing a collagen powder and/or a collagen derivative powder, wherein the hydrophilic organic solvent is an alcohol, a ketone, an ether or a mixture thereof.

Moreover, in the present invention, when a collagen and/or a collagen derivative are allowed to associate with each other in a solution thereof to form a collagen precipitate and/or a collagen derivative precipitate, by adding a salt to the above-described solution of the collagen and/or the collagen derivative while stirring the solution so as to allow the collagen and/or the collagen derivative to be precipitated due to salt precipitation or by adjusting the pH of the solution of the collagen and/or the collagen derivative in the range of 3.5 to 10 to allow the collagen and/or the collagen derivative to be isoelectrically precipitated while stirring the solution, the particle size of the resulting collagen precipitate and/or collagen derivative precipitate can be adjusted.

Effects of the Invention

The collagen powder and/or the collagen derivative powder obtained by the production method according to the present invention have excellent thermal stability and storage stability. In addition, a solution of the collagen powder and/or the collagen derivative powder imparts excellent moisture-retaining properties to skins and the like since the collagen and/or the collagen derivative maintain a triple-helix structure.

The collagen powder and/or the collagen derivative powder according to the present invention have superior transport efficiency as compared to such a solution, so that the costs for storage and transportation can be reduced. Furthermore, since those solutions of collagen or the like are highly viscous, when such solutions are transferred out of a container, for example, adhesion, residue formation and/or loss of the content may occur in the container; however, the collagen powder avoids these problems and can be conveniently handled.

In the collagen powder production method according to the present invention, since the concentration of the collagen precipitate and/or the collagen derivative precipitate in the crude collagen precipitate is 12 to 50% by mass, the crude collagen precipitate can be easily dehydrated with a hydrophilic organic solvent and air-dried, so that a collagen powder and/or a collagen derivative powder are extremely easily produced.

MODE FOR CARRYING OUT THE INVENTION

Figure 1:
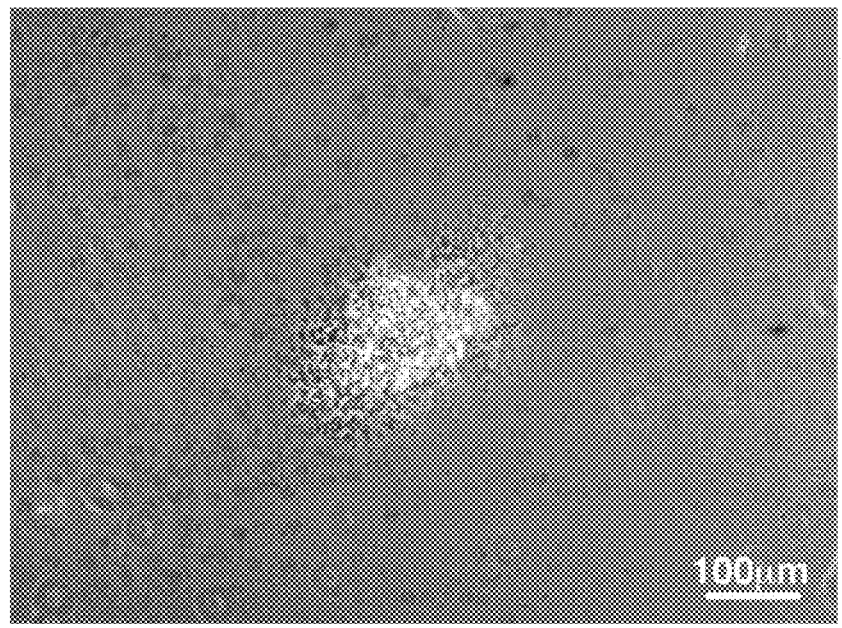
FIG. 1 is a phase contrast microscopic image of the collagen precipitate prepared in Example 1.

The first embodiment of the present invention is a collagen powder and/or a collagen derivative powder, which are obtained by dispersing in a hydrophilic organic solvent a crude collagen precipitate which comprises 12 to 50% by mass of a collagen precipitate and/or a collagen derivative precipitate having an average particle size of 1 to 1,000 µm, recovering solids and then drying the thus recovered solids.

Further, the second and third embodiments of the present invention are each a method of producing a collagen powder and/or a collagen derivative powder, which is characterized by comprising the steps of: obtaining isoelectric precipitates having an average particle size of 1 to 1,000 µm by isoelectrically precipitating a solution containing a collagen and/or a collagen derivative at a pH of 3.5 to 10 while controlling association of the collagen and/or the collagen derivative or by pulverizing the resulting isoelectric precipitates; adjusting the concentration of the resulting collagen precipitate and/or collagen derivative precipitate contained in the above-described isoelectric precipitates to prepare a crude collagen precipitate containing 12 to 50% by mass of the collagen precipitate and/or the collagen derivative precipitate; dispersing the thus obtained crude collagen precipitate in a hydrophilic organic solvent; recovering solids; and drying the thus recovered solids.

Further, the fourth and fifth embodiments of the present invention are each a method of producing a collagen powder and/or a collagen derivative powder, which is characterized by comprising the steps of: obtaining salt precipitates having an average particle size of 1 to 1,000 µm by subjecting a solution containing a collagen and/or a collagen derivative to salt precipitation while controlling association of the collagen and/or the collagen derivative or by pulverizing the resulting salt precipitates; adjusting the concentration of the resulting collagen precipitate and/or collagen derivative precipitate contained in the above-described salt precipitates to 12 to 50% by mass, thereby preparing a crude collagen precipitate; dispersing the thus obtained crude collagen precipitate in a hydrophilic organic solvent; recovering solids; and drying the thus recovered solids. The present invention will now be described in detail.

(1) Collagen and/or Collagen Derivative

The term "collagen" used herein is a general term for a type of protein which has a helical structure formed by three polypeptide strands. Conventionally, type I to type XXIX collagens are known. The collagen used in the present invention may be any of these collagens or a newly discovered collagen. The majority of collagen is insoluble in a living body such as animal skins and bones and, in the present invention, those insoluble collagens are treated with an enzyme such as protease or an alkali and then the resulting collagen solution is collectively referred to as "solubilized collagens". It is noted here that biological materials such as animal skins and bones also contain a trace amount of collagens that are soluble in a neutral salt solution and/or an acid solution. The collagen used in the present invention may be any collagen obtained by solubilizing insoluble collagen or any soluble collagen intrinsically contained in a biological material, as long as the collagen can be dissolved in an aqueous solution. In the present specification, the present invention is described in reference to a "solubilized collagen" prepared by using, as a starting material, insoluble collagen existing in a large amount in a living body; however, the term "collagen" used herein encompasses both "soluble collagen" and "solubilized collagen". Further, the term "collagen fiber" means an association formed by a plurality of "collagen molecules". The "collagen molecules" correspond to the above-described solubilized collagens and soluble collagens. When a solubilized collagen solution is subjected to isoelectric precipitation or salt precipitation, collagen molecules associate with each other, thereby a collagen fiber can be recovered in the form of precipitates. During the precipitation, a plurality of collagen fibers may associate with each other to be precipitated in the form of a large aggregate. Therefore, the term "association" used herein encompasses both a binding of collagen molecules and a binding of collagen fibers. Further, the term "collagen precipitate" means a collagen precipitated out of a collagen solution in the form of a solid and the term "collagen powder" means a "powdery solid of a collagen precipitate".

Here, in "solubilized collagens" and "soluble collagens", their constituent amino acids are modified by a chemical treatment. Therefore, the term "collagen" used herein also encompasses, for example, those collagens in which an asparagine residue, a glutamine residue and/or the like are modified by deamidation reaction caused by an alkali treatment into an asparatic acid residue, a glutamic acid residue and/or the like, respectively. In other words, by modifying an amide group contained in a collagen molecule into a carboxyl group to allow the collagen to have a negative effective charge, the isoelectric point is adjusted to be in the acidic or neutral range. For example, in alkali-solubilized collagen, an asparagine residue and glutamine residue are modified by deamidation reaction caused by an alkali into an asparatic acid residue and a glutamic acid residue, respectively, so that the isoelectric point is shifted to an acidic pH of 4.5 to 6.0. In the present invention, the collagen may be one in which one or more constituent amino acids are modified in this manner.

Further, the term "collagen derivative" used in the present invention means one in which one or more amino acids constituting the above-described collagen are modified with other functional group. Examples of such "collagen derivative" include acylated collagens and esterified collagens. Here, in addition to acylated collagens and esterified collagens that are prepared in advance, the collagen derivative may alternatively be a collagen which is esterified or acylated at the time of salt precipitation or isoelectric precipitation. Prior to the step of extracting a solubilized collagen or a soluble collagen from a collagen-containing tissue, collagen fibers may be acylated for adjustment of the isoelectric point. Also, as a method of producing an esterified collagen, there are cases where insoluble collagen fibers contained in a collagen-containing tissue are esterified in advance and the resulting esterified collagen is isoelectrically precipitated and then recovered. Examples of such acylated collagens and esterified collagens include the ones listed below.

(i) Acylated Collagen

Examples of the acylated collagens include succinylated collagens, phthalated collagens and maleylated collagens. Examples also include acylated collagens such as succinylated collagens, phthalated collagens and maleylated collagens that are obtained by adjusting an atelocollagen solution extracted by an enzyme treatment to have a pH of 9 to 12 and then adding thereto an acid anhydride such as succinic acid, phthalic anhydride or maleic anhydride.

(ii) Esterified Collagen

Examples of the esterified collagens include, in addition to solubilized collagens that are esterified, insoluble collagen fibers that are esterified and then solubilized by an enzyme reaction or the like.

As an alcohol which is allowed to react with a collagen to obtain an esterified collagen, in addition to a primary alcohol, a secondary alcohol or a tertiary alcohol may be employed as well. Further, the alcohol is not restricted to a monohydric alcohol and it may be a dihydric alcohol, a trihydric alcohol or other polyhydric alcohol.

Examples of the monohydric alcohol include methanol, ethanol, 1-propanol, 2-propanol, 1-butanol, dl-2-butanol, tert-butanol, 1-pentanol, dl-2-pentanol, 3-pentanol, 1-hexanol, dl-2-hexanol, dl-3-hexanol, 1-heptanol, 2-heptanol, 3-heptanol, 1-octanol, dl-2-octanol, 3-octanol, 1-nonanol, 2-nonanol, 3-nonanol, 4-nonanol, 5-nonanol, decanol, 1-undecanol, 2-undecanol, ethylene glycol monomethyl ether, ethylene glycol monoethyl ether, ethylene glycol monobutyl ether and ethylene glycol monophenyl ether.

Further, examples of the dihydric alcohol include ethylene glycol, diethylene glycol, triethylene glycol, tetraethylene glycol, polyethylene glycol (M.W.: 200 to 20,000), propylene glycol, 1,3-propanediol, dipropylene glycol, glycerin, 1,2-butanediol, 1,3-butanediol, 1,4-butanediol, 2,3-butanediol, 1,5-pentanediol, 2,4-pentanediol, 1,6-hexanediol and 2,5-hexanediol. Examples of other polyhydric alcohol include glycerin and a variety of sugar alcohols.

The collagen derivative and collagen used in the present invention have a triple-helix structure in a solution.

(2) Crude Collagen Precipitate

The crude collagen precipitate used in the present invention is "a crude collagen precipitate which comprises 12 to 50% by mass of a collagen precipitate and/or collagen derivative precipitate having an average particle size of 1 to 1,000 µm".

As described in the above, collagen fibers are insoluble in vivo, and solubilized collagens can be prepared by subjecting such insoluble collagens to an enzyme treatment or an alkali treatment. Such solubilized collagens are prepared in an aqueous solution and purified into solid precipitates by salt precipitation or isoelectric precipitation. In the present invention, a collagen precipitate obtained in this manner is used. This is because such collagen precipitate and a collagen powder obtained from the collagen precipitate yield a collagen solution containing collagen having a triple-helix structure when they are redissolved in a solution.

Further, the reason why the average particle size of the collagen precipitate and/or the collagen derivative precipitate to be contained in the crude collagen precipitate is restricted to 1 to 1,000 µm is because it was found that a collagen precipitate can be efficiently dehydrated with a hydrophilic organic solvent and powderized by air-drying and that the resulting powder is a fine collagen powder. Accordingly, in the present invention, a method of controlling the average particle size of a collagen precipitate to be on a smaller size was also discovered. It is estimated that when a solubilized collagen solution is subjected to isoelectric precipitation or salt precipitation, collagen molecules associate with each other to form collagen fibers and these collagen fibers further associate with each other to form aggregates, so that the average particles size of the resulting precipitates generally becomes about 2,000 µm or larger. However, by preparing collagen precipitates while controlling the association of collagens by stirring the collagen solution, the average particle size of the resulting collagen precipitates can be controlled at 1 to 1,000 µm and ultimately, a collagen powder having an average particle size of 1 to 1,000 µm can be obtained.

(i) Average Particle Size

The collagen precipitate used in the presently claimed invention has an average particle size of 1 to 1,000 µm, more preferably 5 to 900 µm, particularly preferably 10 to 750 µm, still more preferably 30 to 500 µm. When the average particle size exceeds 1,000 µm, it may become difficult to powderize the crude collagen precipitate. Here, since the length of a collagen molecule is 300 nm, in cases where collagen molecules do not associate with each other, the particle size of the collagen is 300 nm. However, as described below, in SLS collagen formed by a plurality of such 300-nm collagen molecules that are bound with each other in parallel, it was found that SLS collagen associate with each other to form aggregates, thereby yielding precipitates. For such precipitates of SLS collagen, the lower limit of the average particle size was defined to be 1 µm, assuming that at least three SLS collagen are in association. It is noted here that, in the presently claimed invention, the average particle size of the collagen precipitate is a value observed under a phase contrast microscope. In the presently claimed invention, the length of long axis of the collagen precipitate determined on a phase contrast microscopic image was defined as the particle size, and the average particle size was determined by taking an average of particle sizes of all collagen precipitates contained in 10 fields of view.

In the preparation of the crude collagen precipitate, in order to control the constituent collagen precipitate and/or collagen derivative precipitate to have a small particle size, a solution dissolving a solubilized collagen and/or a collagen derivative can be subjected to a physical treatment or a chemical treatment, or generated precipitates can be physically pulverized.

(i-1) Physical Treatment

Examples of the physical treatment method include a method in which a solution dissolving a collagen and/or a collagen derivative is subjected to salt precipitation with stirring and a method in which such a solution is isoelectrically precipitated at a pH of 3.5 to 10 with stirring. The stirring may inhibit association of collagen molecules to allow short collagen fibers to be produced. The stirring can also inhibit the generation of aggregates formed by association of a plurality of collagen fibers. In addition, by pulverizing the generated precipitates, collagen precipitates having a small particle size can be precipitated. The degree of stirring can be selected as appropriate in accordance with, for example, the concentration of the collagen and/or the collagen derivative contained in the solution, the stirring method, and the shape and size of the stirring vessel. Furthermore, in order to inhibit the generation of aggregates caused by association of collagen fibers or efficiently pulverize the generated precipitates, it is also possible to use an apparatus equipped with a stirring mechanism and a pulverization mechanism.

(i-2) Chemical Treatment

Examples of the chemical treatment method include a method in which an association inhibitor which prevents collagen molecules from associating with each other is added. Examples of the association inhibitor include sugars such as glucose, sucrose, xylose, galactose, fructose and glycerin. Another example of the association inhibitor is ATP which allows collagen molecules to form a bundle-like assembly. For example, by adding adenosine triphosphate (ATP) to a collagen solution under acidic condition, the basic moieties of collagen molecules are cross-linked via the phosphate groups of ATP. A plurality of collagen molecules are cross-linked in parallel to each other by ATP, so that a SLS (Segment-Long-Spacing) fiber in which the basic moieties of collagen molecules are cross-linked with each other via the phosphate groups of ATP is generated. In other words, since the cross-linking of collagen molecules by ATP occurs in preference to the above-described association of collagen molecules caused by hydrophobic interactions, a SLS fiber having an average particle size of 300 nm in which 300 nm-long collagen molecules are connected in parallel is formed. Here, a plurality of SLS collagen associate with each other to form an aggregate which is subsequently precipitated. A SLS fiber contains ATP as a cross-linking agent in addition to a collagen; however, a SLS fiber can be powderized in the same manner as in the case of other collagens and collagen derivatives while containing ATP. Alternatively, after obtaining precipitates of SLS fiber, ATP may be removed and then the precipitates may be powderized.

(ii) Collagen Concentration

In the crude collagen precipitate, the concentration of the above-described collagen precipitate and/or collagen derivative precipitate having an average particle size of 1 to 1,000 µm is 12 to 50% by mass, more preferably 15 to 40% by mass, particularly preferably 20 to 35% by mass. When the concentration is lower than 12% by mass, since the water content of the crude collagen precipitate becomes excessively high, the efficiency of dehydration by a hydrophilic organic solvent becomes low, so that drying of the crude collagen precipitate may result in formation of a film-form collagen, rather than a fine and porous collagen powder. Meanwhile, it is not easy to prepare a crude collagen precipitate having a concentration of 50% by mass or higher and such a crude collagen precipitate may not be uniformly dispersed in a hydrophilic organic solvent. It is noted here that, in addition to a collagen precipitate and/or a collagen derivative precipitate, the crude collagen precipitate also comprises other main components, which are aqueous solutions constituting a collagen solution and a collagen derivative solution prior to the precipitation.

(iii) Method of Preparing Crude Collagen Precipitate

In the present invention, a crude collagen precipitate obtained by isoelectric precipitation or salt precipitation can be employed as a starting material. In the step of preparing isoelectric precipitates, salt precipitation is also performed; therefore, in the followings, the method of preparing a crude collagen precipitate will be described in terms of a case where isoelectric precipitates are prepared. Moreover, in the present invention, any of type I to type XXIX collagens can be employed; however, the method of preparing a crude collagen precipitate will be described in terms of a case where I-type collagen is extracted from a living body.

The collagen to be used in the present invention can be collected from a skin of an animal such as cattle, pig, bird or fish or other collagen-containing tissue. In general, collagen is contained in large amount in animal connective tissues; however, when such tissues are subjected to a heat treatment, collagen is thermally denatured and its unique triple-helix structure is broken, causing the collagen to be in a gelatinous state. In the present invention, a collagen which is capable of maintaining a triple-helix structure is used. As a method of extracting such a collagen, for example, a solubilization method in which a material such as animal bone or skin is subjected to an alkali treatment, an acid treatment and/or an enzyme treatment can be employed. Preferred examples of the material from which the collagen is extracted include dermises and tendons of cattle, pig, chicken, ostrich, horse, fish and the like. It is preferred to use a young animal tissue such as embryo-derived tissue since the yield is improved.

(iii-1) Crude Collagen Precipitate Having an Isoelectric Point at pH 4.5

For example, as insoluble collagen to be used as a starting material, a lime-immersed split skin which is washed, chopped into an about 10-cm square pieces using a ham slicer, minced and then further mechanically mashed can be employed after delipidation with an organic solvent such as acetone or ether or lipase and subsequent thorough washing.

In a solution obtained by mixing sodium hydroxide at a final concentration of 3% by mass and monomethyl amine at a concentration of 1.9% (v/w), insoluble collagen is suspended to a final concentration of 4.5% by mass, and the resulting suspension is subjected to a solubilization treatment at 18° C. for 3 weeks. After terminating the reaction, salt precipitation is performed by adding a salt such as sodium chloride to a final concentration of 5% by mass. The resulting salt precipitates are redissolved in an aqueous solution adjusted to be acidic with hydrochloric acid and then purified by filtration through, for example, a cloth, a filter paper and/or a metal mesh. Thereafter, by adjusting the thus obtained collagen solution to have a pH of 4.5 with sodium hydroxide, a crude collagen precipitate having an isoelectric point of 4.5 can be obtained.

Here, the average particle size can be adjusted to 1 to 1,000 µm by subjecting the above-described collagen solution to isoelectric precipitation at pH 4.5 or salt precipitation while stirring the collagen solution. Such method of controlling the average particle size is also the same in the following (iii-2), (iii-3) and (iii-4).

(iii-2) Crude Collagen Precipitate Having an Isoelectric Point at pH 9.0

Insoluble collagen, which was obtained by grinding the dermis layer of a bovine skin using a meat grinder or the like, followed by defatting and sufficient washing, can be used as a starting material. After suspending the insoluble collagen in distilled water to a final concentration of 1% by mass, hydrochloric acid is added to the resulting suspension to adjust the pH to 3.0. Then, acidic protease is added in an amount of one-hundredth of the collagen weight, and the resultant is subjected to a solubilization treatment at 25° C. for 72 hours. After terminating the enzyme reaction, to the enzyme-solubilized collagen solution obtained in the above-described manner, sodium chloride is added to a final concentration of 5% by mass to perform salt precipitation, and the resulting precipitates are recovered by centrifugation. The thus recovered salt precipitates are dispersed in distilled water to a collagen concentration of 2% by mass and then uniformly dissolved by adjusting the pH of the resulting dispersion to 3.0 with an addition of hydrochloric acid, thereby obtaining a collagen solution. Then, after filtering the thus obtained collagen solution through a cloth and a filter paper, by adjusting the collagen solution to have a pH of 9.0 with sodium hydroxide, a crude collagen precipitate having an isoelectric point of 9.0 can be obtained.

(iii-3) Crude Collagen Precipitate Having an Isoelectric Point at a pH of 4.5 to 9.0

In an aqueous solution obtained by mixing sodium hydroxide at a final concentration of 3% by mass and monomethyl amine at a concentration of 1.9% (v/w), insoluble collagen or the enzyme-solubilized collagen described in the above (iii-2) is suspended, and the resulting suspension is subjected to an alkali treatment for a desired time, thereby precipitates can be obtained. For example, in cases where the enzyme-solubilized collagen is used as a starting material, a four-hour alkali treatment lowers the isoelectric point to 7.8 and a one-day alkali treatment lowers the isoelectric point to 5.6. Once a desired isoelectric point is attained, the reaction is quenched with an addition of hydrochloric acid, and the resultant is then salt-precipitated by adding thereto sodium chloride to a final concentration of 5% by mass. The resulting precipitates are recovered by centrifugation. The thus recovered salt precipitates are dispersed in distilled water to a collagen concentration of 2% by mass and then uniformly dissolved by adjusting the pH of the resulting dispersion to 3.0 with an addition of hydrochloric acid, thereby obtaining a collagen solution. Then, after filtering the thus obtained collagen solution through a cloth and a filter paper, by adjusting the collagen solution to have an isoelectric point at a desired pH with sodium hydroxide, a crude collagen precipitate having an isoelectric point of 4.5 to 9.0 can be obtained.

(iii-4) Crude Collagen Precipitate Composed of Collagen Derivative

By acylation or esterification of insoluble collagen, the enzyme-solubilized collagen described in the above (iii-2) or the alkali-solubilized collagen described in the above (iii-1), a collagen derivative having an isoelectric point at a pH of 4.5 to 9.0 can be obtained. Here, esterification can also be performed by inducing the carboxyl group in the collagen molecule to carboxylic acid chloride so as to perform dehydrochlorination reaction between the hydroxyl group of the above-described alcohol and acid chloride.

For example, when enzyme-solubilized collagen having an isoelectric point of 9.0 is acylated, the amino group of the collagen is modified and the isoelectric point is consequently shifted to the acidic side. Further, when alkali-solubilized collagen having an isoelectric point of 4.5 is esterified, the carboxyl group of the collagen is modified and the isoelectric point is consequently shifted to the basic side. Thus, once a desired isoelectric point is attained, salt precipitation is performed by adding sodium chloride to a final concentration of 5% by mass and the resulting precipitates are recovered by centrifugation. The thus recovered salt precipitates are dispersed in distilled water to a collagen concentration of 2% by mass and then uniformly dissolved by adjusting the pH of the resulting dispersion to 3.0 with an addition of hydrochloric acid, thereby obtaining a collagen solution. Then, after filtering the thus obtained collagen solution through a cloth and a filter paper, by adjusting the collagen solution to have an isoelectric point at a desired pH with sodium hydroxide, a crude collagen precipitate having an isoelectric point of 4.5 to 9.0 can be obtained.

(iv) Isoelectric Point

The isoelectric points of a collagen and a collagen derivative can be adjusted by, for example, a solubilization method. In the present invention, the isoelectric precipitate corresponds to a collagen and/or a collagen that are derivative obtained by adjusting the pH of the above-described collagen and/or collagen derivative solutions to 3.5 to 10. The term "isoelectric point" means the pH of a solution at which a collagen and/or a collagen derivative show the minimum solubility in an aqueous solution containing the collagen and/or the collagen derivative. The isoelectric point of collagen is generally at pH 4.3 to 9.3; however, since precipitates may be formed even in a solution having a pH of lower than 4.3 or higher than 9.3, the isoelectric precipitate is defined to be a collagen and/or a collagen derivative that are obtained by adjusting the pH of the above-described collagen and/or collagen derivative solution to 3.5 to 10. The isoelectric precipitate has an isoelectric point at a pH of more preferably 4.0 to 9.0, particularly preferably 4.5 to 9.0. Furthermore, an isoelectric precipitate having an isoelectric point at a pH of 3.5 to 8.0, 3.5 to 7.0, 3.5 to 6.0 or 4.5 to 5.0 may also be employed in accordance with the application thereof. As shown in the later-described Examples, even when the average particle size of the collagen powder according to the present invention is large, the collagen powder has a specific surface area which is substantially the same as that of a very fine particle. Therefore, the collagen powder is believed to exhibit excellent solubility even in a neutral solution where solubility is intrinsically poor.

The crude collagen precipitate recovered by adjusting the pH of a collagen and/or a collagen derivative-containing solution to 4.5 has an isoelectric point at pH 4.5 and the one recovered by adjusting the pH of a collagen and/or collagen derivative-containing solution to 9.0 has an isoelectric point at pH 9.0.

In the present invention, the "crude collagen precipitate" to be dispersed in a hydrophilic organic solvent is not restricted to a crude collagen precipitate having an isoelectric point at pH 4.5 and a crude collagen precipitate having an isoelectric point at pH 9.0. Depending on the application, for example, a mixture of a crude collagen precipitate having an isoelectric point at pH 4.5 and a crude collagen precipitate having an isoelectric point at pH 9.0 may also be employed. This is because, regardless of the isoelectric point, as long as the concentration of the above-described collagen precipitate and/or collagen derivative precipitate that are contained in the crude collagen precipitate is 12 to 50% by mass, the collagen precipitate and/or the collagen derivative precipitate can be uniformly dispersed in a hydrophilic organic solvent and thereby a fine collagen powder and/or a fine collagen derivative powder can be produced.

(2) Hydrophilic Organic Solvent

The hydrophilic organic solvent in which the above-described crude collagen precipitate is dispersed may be any carbon-containing solvent miscible with water and it is not particularly restricted. Examples of such hydrophilic organic solvent include alcohols, ketones, ethers, esters and polar aprotic solvents.

Examples of the alcohols include monohydric alcohols having 1 to 6 carbon atoms, such as methanol, ethanol, isopropanol and t-butanol; and polyhydric alcohols such as ethylene glycol and propylene glycol. Examples of the ketones include acetone and methyl ethyl ketone. Further, examples of the ethers include glycol ethers such as diethyl ether, methylethyl ether, ethylene glycol monomethyl ether and diethylene glycol monobutyl ether; and cyclic ethers such as tetrahydrofuran and dioxane. Moreover, examples of the esters include ethyl acetate and ethyl lactate, and examples of the polar aprotic solvents include dimethyl sulfoxide (DMSO), dimethylformamide (DMF) and pyridine. Thereamong, preferred examples of solvents that are miscible with water at an arbitrary ratio include acetone, methanol, ethanol, isopropanol, acetonitrile, tetrahydrofuran, dimethyl sulfoxide and dimethylformamide. Among these solvents, ethanol, acetone, diethyl ether or a mixture thereof can be suitably used.

The amount of the hydrophilic organic solvent to be used can be selected as appropriate in accordance with the type thereof. For example, in cases where ethanol is used, it is preferred that ethanol be added in an amount of 3 to 2,000 parts by mass, preferably 5 to 1,000 parts by mass, more preferably 10 to 100 parts by mass, particularly preferably 10 to 30 parts by mass, with respect to 1 part by mass of the above-described crude collagen precipitate.

(3) Collagen Powder and Collagen Derivative Powder

The collagen powder and/or the collagen derivative powder according to the present invention can be obtained by dispersing the above-described crude collagen precipitate in a hydrophilic organic solvent, recovering the resulting solids and then drying the thus recovered solids. The collagen powder and/or the collagen derivative powder according to the present invention are those which are obtained by dehydrating the crude collagen precipitate with a hydrophilic organic solvent and then drying the resulting solids.

The above-described crude collagen precipitate is adjusted to have a specific isoelectric point by isoelectric precipitation. Since this isoelectric point is not shifted by the dehydration with a hydrophilic organic solvent and the subsequent drying, the isoelectric point of the collagen powder and/or the collagen derivative powder according to the present invention is dependent on the isoelectric point in the isoelectric precipitation. When a crude collagen precipitate having an isoelectric point at pH 4.5 is used, the resulting collagen powder and/or collagen derivative powder have an isoelectric point at pH 4.5, and when a crude collagen precipitate having an isoelectric point at pH 9.0 is used, the resulting collagen powder and/or collagen derivative powder have an isoelectric point at pH 9.0. Further, for example, when a mixture of collagens and/or collagen derivatives having an isoelectric point at a pH of 4.5 to 9.0 is used, the resulting collagen powder and/or collagen derivative powder have an isoelectric point at a pH of 4.5 to 9.0.

The collagen powder and/or the collagen derivative powder according to the present invention have an isoelectric point at a pH of 3.5 to 8.0, more preferably at a pH of 3.5 to 7.0. In particular, in cases where the collagen powder and/or the collagen derivative powder have an isoelectric point at a pH of 3.5 to 6.0, the initial dissolution rate of a pH 6.5 solution containing 5 mg of the powder(s) is not lower than 0.2 mg/min, more preferably not lower than 0.3 mg/min, particularly preferably not lower than 0.5 mg/min. It is noted here that, in the present invention, the "initial dissolution rate" is measured by the method described in Examples below.

In conventional collagens having an isoelectric point at a pH of 3.5 to 8.0, the solubility thereof in a neutral solution is not sufficient; therefore, it is required that such collagens be once dissolved in a solution having a pH more acidic than their isoelectric points and the resulting solution be then adjusted to a pH of 5.5 to 8.5 by an addition of an alkali. In the present invention, for example, in the case of a collagen powder having an isoelectric point at pH 4.5, since such a collagen powder is readily dissolved in a solution having a pH of 5.5 to 8.5, it is not required to be dissolved in a stronger acid, so that the subsequent addition of an alkali is also not necessary. This not only makes the dissolution operations simple, but also enables to avoid the formation of a salt between an acid and an alkali. Furthermore, since such a collagen is not required to be dissolved in an alkali, denaturation and degradation of the collagen can be avoided and a collagen solution having a high content of triple-helix structure can be produced.

In the present invention, the average particle size of the collagen powder and that of the collagen derivative powder are not restricted; however, by using, for example, a crude collagen precipitate having an average particle size of 1 to 1,000 μm, the collagen powder and the collagen derivative powder ultimately have an average particle size of 8 to 1,000 μm, preferably 10 to 1,000 μm, more preferably 30 to 950 μm, still more preferably 30 to 900 μm, particularly preferably 30 to 800 μm. It is noted here that, in the present specification, the average particle size of the collagen powder and that of the collagen derivative powder are also measured under an electron microscope in the same manner as in the case of the above-described crude collagen precipitate. As described in the above, the average particle size of generally resulting precipitates generally becomes 2,000 μm or larger by association or that of the collagen powder obtained by spray-drying becomes smaller than 5 μm. Since the collagen powder and the collagen derivative powder according to the present invention have an average particle size of 8 to 1,000 μm, they can be prevented from scattering in the air and at the same time, the fluidity can be ensured. Furthermore, as shown in the later-described Examples, when the average particle size of the collagen powder is smaller than 5 μm, the collagen powder may form lumps in a solution to reduce the solubility; however, when the average particle size is in the above-described range, lumps are not formed, so that excellent solubility is attained.

Moreover, it was also discovered that, in the collagen powder and the collagen derivative powder according to the present invention, by dispersing the crude collagen precipitate in a hydrophilic organic solvent, the collagens are finely dispersed in the solvent and the resulting precipitates are porous and have an increased specific surface area. The specific surface area of the collagen powder and the collagen derivative powder according to the present invention is not less than 0.5 m$^2$/g, preferably 0.8 to 30 m$^2$/g, more preferably 1.0 to 25 m$^2$/g, particularly preferably 1.2 to 20 m$^2$/g, still more preferably 1.5 to 20 m$^2$/g. With such a specific surface area, the hydrophilicity and solubility are ensured.

Conventionally, even when a collagen precipitate was dispersed in a hydrophilic organic solvent, if the collagen concentration were low, it was difficult to dehydrate the collagen precipitate with the hydrophilic organic solvent and the precipitate was solidified in the form of a pellet, so that powdery dry product could not be obtained. Further, when a collagen precipitate or a collagen derivative precipitate had a conventional average particle size of 2,000 μm, powderization thereof was difficult. However, in the present invention, since the average particle size of the collagen precipitate and/or the collagen derivative precipitate was managed to be 1 to 1,000 μm and the concentration of the collagen precipitate and/or the collagen derivative precipitate contained in the crude collagen precipitate was controlled at 12 to 50% by mass, the dehydration by a hydrophilic organic solvent could also be performed in a powder form and a collagen powder and/or a collagen derivative powder were obtained by air-drying the recovered solids. Furthermore, it was also discovered that, since the collagen precipitate prior to being dispersed in a hydrophilic organic solvent has an average particle size of 1 to 1,000 μm, air-drying of the collagen precipitate yields a collagen powder having an average particle size of 8 to 1,000 μm. This is believed to be because association and aggregation of collagens are inhibited in the above-described steps of dispersing in a hydrophilic organic solvent and drying. It is noted here that, in the present invention, the above-described collagen derivative powder and/or collagen powder may also be further processed so as to, for example, obtain a more refined powder.

The collagen powder and/or the collagen derivative powder according to the present invention are dried without a heating step; therefore, a collagen maintains a triple-helix structure in a solution when the collagen powder and/or the collagen derivative powder is dissolved. Further, since the collagen powder and/or the collagen derivative powder according to the present invention have excellent heat resistance, they are not required to be refrigerated for storage as in the case of conventional collagen solutions.

Here, when the collagen powder and/or the collagen derivative powder according to the present invention are dissolved, the above-described aggregates are also dissolved in the form of original collagen molecules or collagen derivative molecules. Therefore, by subjecting a solution thereof to isoelectric precipitation or salt precipitation in accordance with a conventional method, a collagen precipitate and/or a collagen derivative precipitate having an average particle size of larger than 1,000 μm, that is, a conventional average particle size of about 2,000 μm, can be generated.

(4) Application

The collagen powder and the collagen derivative powder according to the present invention can be suitably used in, for example, medical applications and cosmetic applications. Examples of the cosmetic applications include cosmetic liquids, milky lotions, liquid foundations, general creams, facial cleansers such as cleansing creams, packs, shaving creams, sunscreen creams, sunscreen lotions, suntan lotions, cosmetic soaps, foundations, face powders, lipsticks, lip balms, shampoos and rinses.

Further, examples of the medical applications include carriers of DDS (Drug Delivery System) used in regenerative medicine, culture substrates for a variety of cells such as ES cells and iPS cells, blood coagulants, therapeutic agents for decubitus ulcer and bone-filling agents.

(5) Production Method

The collagen powder and/or the collagen derivative powder according to the present invention can be produced by: obtaining isoelectric precipitates having an average particle size of 1 to 1,000 μm by isoelectrically precipitating a solution containing a collagen and/or a collagen derivative at a pH of 3.5 to 10 while controlling association of the collagen and/or the collagen derivative; adjusting the concentration of the resulting collagen precipitate and/or collagen derivative precipitate contained in the above-described isoelectric precipitates to prepare a crude collagen precipitate containing 12 to 50% by mass of the collagen precipitate and/or the collagen derivative precipitate; dispersing the thus obtained crude collagen precipitate in a hydrophilic organic solvent; recovering solids; and then drying the thus recovered solids.

Alternatively, the collagen powder and/or the collagen derivative powder according to the present invention can also be produced by: performing salt precipitation instead of the isoelectric precipitation to obtain salt precipitates having an average particle size of 1 to 1,000 μm; adjusting the concentration of the resulting collagen precipitate and/or collagen derivative precipitate contained in the above-described salt precipitates to 12 to 50% by mass so as to prepare a crude collagen precipitate; dispersing the thus obtained crude collagen precipitate in a hydrophilic organic solvent; recovering solids; and then drying the thus recovered solids.

(i) Production of Crude Collagen Precipitate

When a collagen solution is subjected to isoelectric precipitation or salt precipitation, in general, collagen precipitates having an average particle size of about 2,000 μm are formed. However, as described in the above, by inhibiting the association of collagen molecules or by physically pulverizing the precipitates, a crude collagen precipitate composed of a collagen precipitate and/or a collagen derivative precipitate having an average particle size of 1 to 1,000 μm can be prepared.

Here, in cases where the collagen solution is stirred in order to obtain a collagen precipitate having an average particle size of 1 to 1,000 μm, it is preferred that the collagen solution be stirred both before and after the collagen precipitate is generated. Before the generation of the collagen precipitate, association of the collagen molecules can be inhibited to allow short collagen fibers to be formed, and after the generation of the collagen precipitate, association of the collagen fibers can be inhibited, so that the generation of aggregates can be suppressed. Here, in cases where a stone mill-type grinder such as a masscolloider is used, precipitates are pulverized simultaneously with the stirring, and this is preferred because the precipitates that are generated from the collagen solution can be pulverized to have a small particle size. Further, after precipitates are formed by salt precipitation or isoelectric precipitation, the whole dispersion liquid may be added to a stone mill-type grinder or the like to pulverize the precipitates. In this case, since the precipitates are in the solution, precipitates can be pulverized without heating and association of aggregates can be separated, so that the particle size of the precipitates can be made small.

The degree of the stirring and pulverization can be selected as appropriate in accordance with, for example, the concentration of the collagen and/or the collagen derivative contained in the solution, the stirring method, and the shape and size of the stirring vessel. In cases where a homogenizer is used, the rotation speed thereof is 1,000 to 20,000 rpm. The stirring time can be selected as appropriate in accordance with the rotation speed or the like and it is 1 minute to 5 hours. By measuring the actual particle size and changing the stirring intensity, a collagen precipitate and/or a collagen derivative precipitate having a desired average particle size can be obtained. In the present invention, as described in the above, the pulverization of collagen precipitate and/or collagen derivative precipitate is performed in a collagen solution because it does not require the step of separating the precipitates from the solution and the pulverization efficiency is excellent.

In the present invention, as a method of inhibiting association of collagen molecules, the above-described association inhibitor may also be added. For example, when an association inhibitor such as adenosine triphosphate (ATP) is added to a collagen solution under acidic condition, 300 nm-long SLS collagen are formed and aggregates formed by association of a plurality of the SLS collagen can be obtained in the form of precipitates. In the present invention, along with the addition of an association inhibitor, the collagen solution may also be stirred to physically inhibit the association. By the stirring, aggregates of SLS collagen are pulverized, so that the particle size of the resulting precipitates can be adjusted to be shorter.

In the present invention, an isoelectric precipitate comprising a collagen precipitate and/or a collagen derivative precipitate at a concentration of 12 to 50% by mass is used as a crude collagen precipitate. When the concentration of the collagen precipitate and/or collagen derivative precipitate that are contained is less than 12% by mass, the isoelectric precipitate recovered by centrifugation, filtration and the like can be once again desalted by washing with water whose pH is adjusted to be the same as the one used in the isoelectric precipitation and then once again subjected to centrifugation, filtration and the like before being used as a crude collagen precipitate.

In the same manner, in cases where the precipitate was formed by salt precipitation, it can be washed again with water having the same salt concentration as in the salt precipitation and then once again subjected to centrifugation, filtration and the like before being used as a crude collagen precipitate. Here, in cases where the above-described concentration was achieved by a single round of centrifugation, filtration and the like of the resulting isoelectric precipitate or salt precipitate, these centrifugation and filtration processes also serve as a concentration-adjusting step at the same time; therefore, it is not necessary to perform a particular concentration-adjusting step.

(ii) Dispersion in Hydrophilic Organic Solvent

In the present invention, a crude collagen precipitate obtained in the above-described manner is dispersed in the above-described hydrophilic organic solvent. By this, the crude collagen composition is dehydrated. The temperature of the hydrophilic organic solvent to be used is preferably not higher than 15° C. This is because the solubilized collagen and/or the collagen derivative are not denatured and are allowed to retain a triple-helix structure.

The amount of the above-described hydrophilic organic solvent to be used with respect to that of the crude collagen precipitate can be selected as appropriate in accordance with the type of the hydrophilic organic solvent to be used. For example, in cases where ethanol is used, it is preferred that ethanol be added in an amount of 3 to 2,000 parts by mass, preferably 5 to 1,000 parts by mass, more preferably 10 to 100 parts by mass, particularly preferably 10 to 30 parts by mass, with respect to 1 part by mass of the above-described crude collagen precipitate.

In the hydrophilic organic solvent in which the crude collagen precipitate is dispersed, the concentration of the hydrophilic organic solvent is preferably not lower than 75% by mass, more preferably not lower than 90% by mass, still more preferably not lower than 95%. When the concentration of the hydrophilic organic solvent in a hydrophilic organic solvent dispersion dispersing the crude collagen precipitate in the hydrophilic organic solvent is lower than 75% by mass, since the collagens recovered therefrom contain moisture, it requires a long time to dry the collagens. Also, since the collagen molecules adhere to each other during the drying, a fine and porous collagen powder and/or collagen derivative powder may not be attained.

After dispersing the crude collagen precipitate in the hydrophilic organic solvent, the resulting dispersion may also be stirred. For example, in cases where a homogenizer is used, the stirring is performed at a rotation speed of 1,000 to 20,000 rpm, more preferably 2,000 to 13,000 rpm, particularly preferably 2,500 to 10,000 rpm, still more preferably 3,000 to 5,000 rpm. The stirring time can be selected as appropriate in accordance with the rotation speed or the like. The stirring time is 1 minute to 5 hours, more preferably 1 minute to 3 hours, particularly preferably 3 minutes to 1 hour, still more preferably 5 minutes to 30 minutes. It is noted here, however, that the above-described stirring conditions are described for exemplary purposes and that the stirring conditions are variable depending on the stirring method of a given stirring apparatus. The stirring conditions can be selected as appropriate in accordance with the actual degree of dispersion. Since heat is generated by the stirring, it is preferred that the stirring be performed while cooling the dispersion.

(iii) Recovery of Solids

The crude collagen precipitate dispersed in the hydrophilic organic solvent precipitates in the solvent. In the present invention, in order to recover this precipitate, the hydrophilic organic solvent dispersion is filtered. Alternatively, the collagen precipitate is recovered by a separation means such as centrifugation.

Such dispersion by the hydrophilic organic solvent and recovery are sufficiently performed once; however, these processes may be performed a plurality of times, for example, twice or three times.

(iv) Drying

In the present invention, a collagen powder and/or a collagen derivative powder can be obtained by drying the above-described solids. The present invention is characterized in that the above-described solids can be air-dried at room temperature. However, the drying may also be performed by other method such as the use of a dryer. In this case, the temperature is preferably set at lower than 15° C.

It is thought that, since the collagen precipitate and/or the collagen derivative precipitate constituting the above-described crude collagen precipitate have a smaller average particle size of 1 to 1,000 μm as compared to conventional ones, the surface area thereof per unit mass is large, so that the collagen precipitate and/or the collagen derivative precipitate are easily dehydrated by the hydrophilic organic solvent. It is also thought that, since the concentration of the collagen precipitate and/or the collagen derivative precipitate contained in the crude collagen precipitate is 12 to 50% by mass, the amount of water contained in the hydrophilic organic solvent is reduced and consequently, the collagen precipitate and/or the collagen derivative precipitate can thus be powderized by air-drying. Furthermore, since the drying of the collagen precipitate and/or the collagen derivative precipitate can be achieved by air-drying, it is not required to perform a heat treatment, so that thermal denaturation of the collagen powder and/or the collagen derivative powder can prevented. Consequently, the collagen powder and/or the collagen derivative powder exhibit a triple-helix structure. It is noted here that, in the present invention, the collagen powder and/or the collagen derivative powder obtained in this manner may further be pulverized using a mill or the like to adjust the particle size thereof.

Conventionally, as a purification method of collagen, there are known, for example, a salt precipitation method in which an acidic collagen solution is precipitated by adding thereto a salt, an organic solvent precipitation method in which an organic solvent is added and an isoelectric precipitation method in which an acid or an alkali is added. However, there has not been a case where a collagen was powderized by adding a hydrophilic organic solvent to an isoelectric precipitate or salt precipitate of a collagen solution having an isoelectric point at a pH of 3.5 to 10. The reason for this is because collagen is highly hydrophilic by nature and an isoelectric precipitate thereof also contains a large amount of water, so that a solid of collagen is generally obtained by freeze-drying, spray-drying or the like. If anything, in Comparative Example 1 of the above-described Patent Literature 6, an attempt was made to perform ethanol washing on a collagen precipitate obtained by salt precipitation of an atelocollagen; however, it is described that the collagen precipitate could not be dehydrated since the resulting collagen aggregates included sodium chloride-containing water. However, in the present invention, by controlling the collagen precipitate and/or the collagen derivative precipitate that are contained in an isoelectric precipitate or salt precipitate to have an average particle size of 1 to 1,000 μm, the collagen precipitate and/or the collagen derivative precipitate can be easily dispersed in a hydrophilic organic solvent and, by controlling the concentration of the above-described collagen precipitate in the crude collagen precipitate at 12 to 50% by mass, dehydration thereof by a hydrophilic organic solvent can be efficiently carried out. Consequently, the solids recovered from the hydrophilic organic solvent can be adjusted to have extremely low water content and a fine collagen powder and/or collagen derivative powder can be prepared by drying the recovered solids at room temperature.

Here, a dry collagen can be obtained by drying a collagen solution at room temperature for a prolonged period of time; however, since the collagen and/or the collagen derivative adhere to the container wall and the like, the resulting dry collagen is in the form of a film, plate, or block. A characteristic feature of the present invention resides in that a collagen powder can be obtained by air-drying. Furthermore, when a solution having a collagen concentration of 0.1 to 10% by mass is charged into a hydrophilic organic solvent via an injection opening of a nozzle to allow collagen thread to be precipitated, pores are not formed on the surface of the resulting collagen thread and a film-form collagen with a smooth surface is produced.

EXAMPLES

The present invention will now be described concretely by way of examples thereof; however, the present invention is not restricted thereto by any means.

Example 1

(1) Insoluble collagen fiber, which was obtained by grinding the dermis layer of a porcine skin using a meat grinder or the like, followed by defatting and sufficient washing, was used as a starting material. In a solubilized aqueous solution in which sodium hydroxide and monomethyl amine were mixed to final concentrations of 3% by mass and 1.9% (v/w), respectively, the insoluble collagen prepared to have a collagen final concentration of 4.5% by mass was suspended, and the resultant was subjected to a solubilization treatment at 18° C. for 3 weeks. To the resulting alkali-solubilized collagen solution obtained in the above-described manner, sodium chloride was added to a final concentration of 5% by mass to perform salt precipitation, and the resultant was centrifuged to recover precipitates. The thus recovered salt precipitates were dispersed in distilled water to a collagen concentration of 3% by mass and then uniformly dissolved by adjusting the pH of the resulting dispersion to 3.0 with an addition of hydrochloric acid. Then, after filtering the thus obtained solution through a piece of cloth and a filter paper, the filtered solution was adjusted with sodium hydroxide to have a pH of 4.5 and collagen was isoelectrically precipitated while stirring the solution using a masscolloider (stone mill-type grinder: manufactured by Masuko Sangyo Co., Ltd.) at a flow rate of 500 ml/min, a rotation speed of 1,500 rpm and a clearance of 50 μm. The collagen precipitates contained in the thus obtained precipitates had an average particle size of 141 μm. Subsequently, the solution was centrifuged at 17,500 rpm for 20 minutes to recover precipitates and then washed again for desalting with distilled water adjusted to have a pH of 4.5. The resulting solution was subjected to 10 rounds of the above-described centrifugation and precipitates were recovered as a crude collagen precipitate. This crude collagen precipitate had a collagen concentration of 30% by mass. FIG. 1 shows a phase contrast microscopic image of the thus obtained collagen precipitate.

Then, 50 g of the thus obtained crude collagen precipitate was added to 950 g of ethanol with a temperature of 20° C. and dispersed for 30 minutes using a homogenizer. The resulting dispersion was filtered to recover solid collagen, which was then air-dried at room temperature to obtain a collagen powder. The properties, isoelectric point, success or failure of powderization and the like of the thus obtained collagen are shown in Table 1.

Figure 2:
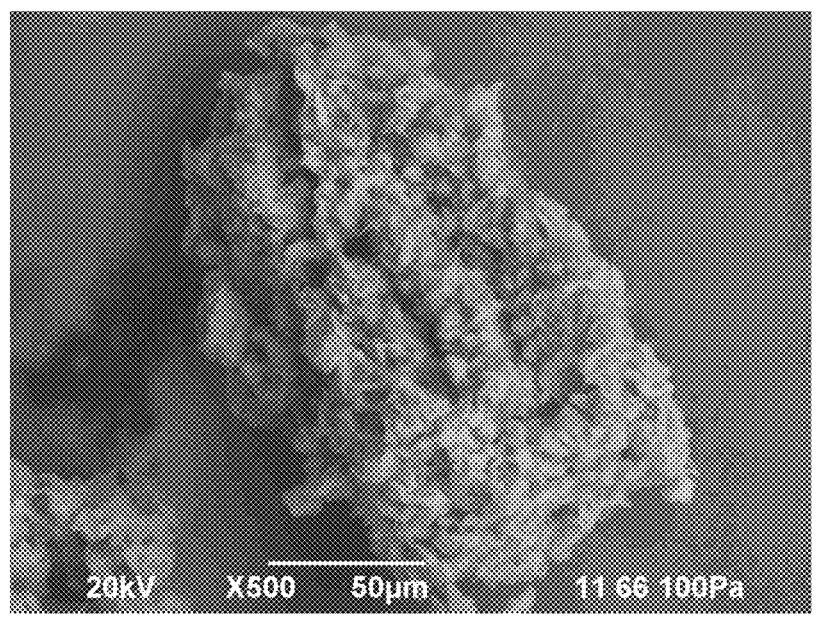
FIG. 2 is a scanning electron microscopic image of the collagen powder prepared in Example 1.
Figure 3:
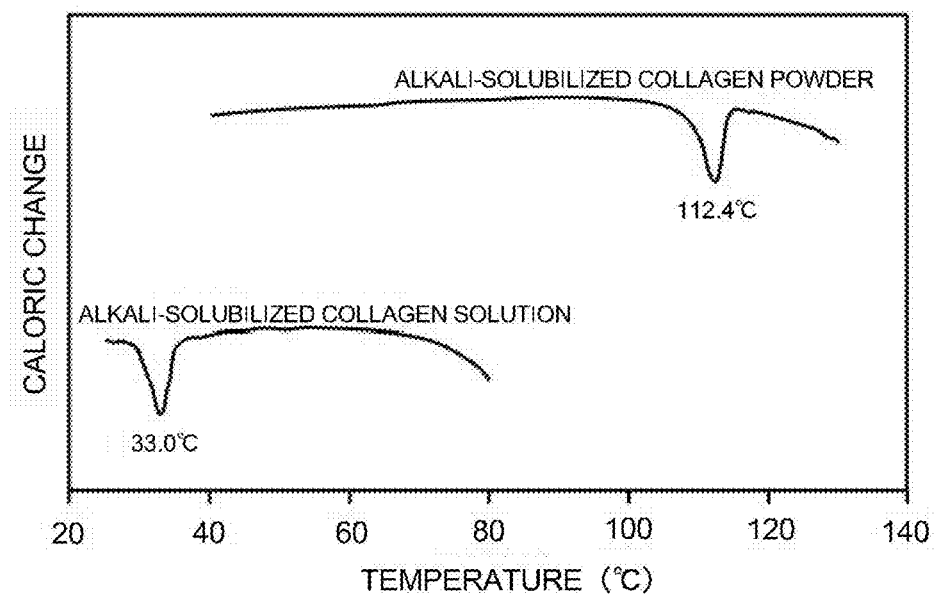
FIG. 3 is a graph showing the results of the measurements performed by a differential scanning calorimeter (DSC) for the collagen powder prepared in Example 1.

(2) The thus obtained collagen powder was observed under a scanning electron microscopic image. The result of the observation is shown in FIG. 2. It was found that the collagen powder was uneven and porous, and had an average particle size of 158 mm (3) The denaturation temperature of the thus obtained collagen powder was measured by a differential scanning calorimeter (DSC). The results are shown in FIG. 3 and Table 2. The results for the alkali-solubilized collagen solution which was obtained in Example 1 as a control are also shown. The powder collagen was observed to have a peak of large caloric change at 112° C.

Figure 4:
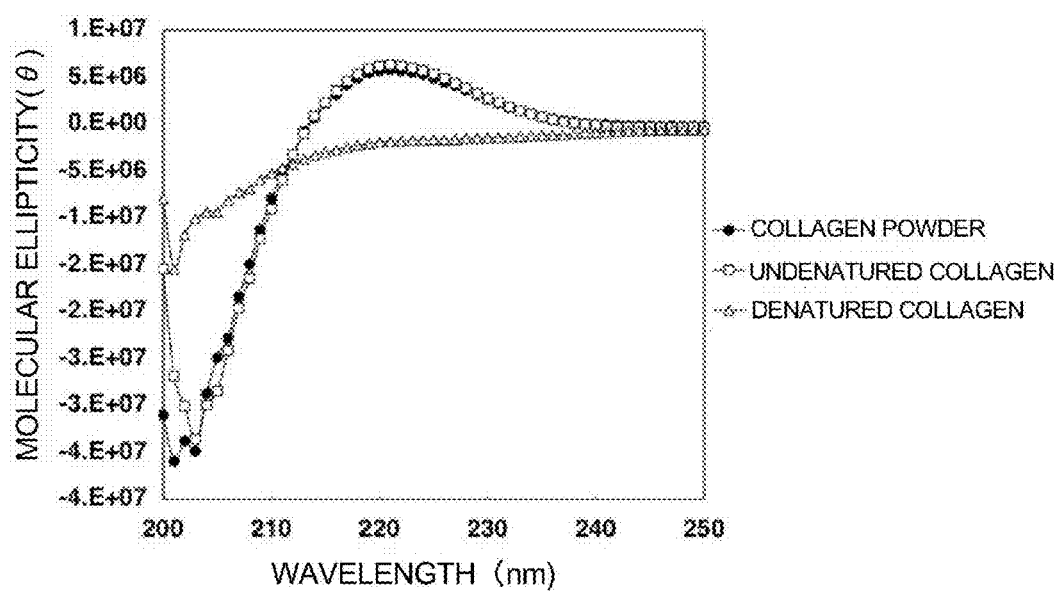
FIG. 4 is a graph showing the circular dichroism of the collagen solution in which the powder collagen prepared in Example 1 was redissolved.

(4) Then, 5 mg of the thus obtained collagen powder was redissolved in 1 ml of 10 mM acetic acid and the resultant was adjusted with 5 mM acetic acid to prepare a collagen solution having a final concentration of 0.1 mg/ml. The circular dichroism (CD) of the thus obtained collagen solution was measured at 20° C. The results are shown in FIG. 4. FIG. 4 also shows the results for the alkali-solubilized collagen solution (undenatured collagen) which was obtained in Example 1 as a control and the results for a heat-denatured collagen solution (denatured collagen) which was obtained by thermally denaturing the above-described alkali-solubilized collagen solution at a temperature of 100° C. for 3 minutes. The curve of the redissolved collagen solution (the collagen powder of the present invention) was substantially identical to that of the undenatured collagen; therefore, it was found that the redissolved collagen solution retained a triple-helix structure at 20° C.

(5) Using a vibration dryer (VU-45; manufactured by Chuo Kakohki Co., Ltd.), the solid collagen prepared in the above (1) was dried for 4 hours at a degree of vacuum of 40 Torr and a drying temperature of 40° C. to obtain a collagen powder. For the thus obtained collagen powder, using a four-sample specific surface area-pore distribution measuring apparatus (manufactured by Quantachrome Instruments, trade name: "Model NOVA-4200e"), the specific surface area was measured by a single-point BET method. The result is shown in Table 3.

Figure 5:
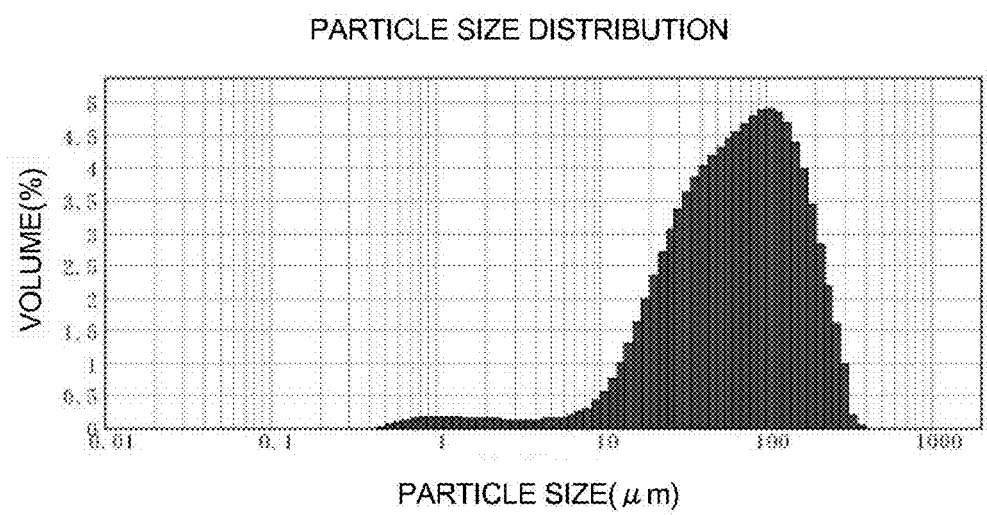
FIG. 5 is a graph showing the particle size distribution of the collagen powder obtained in Example 1.
Figure 6:
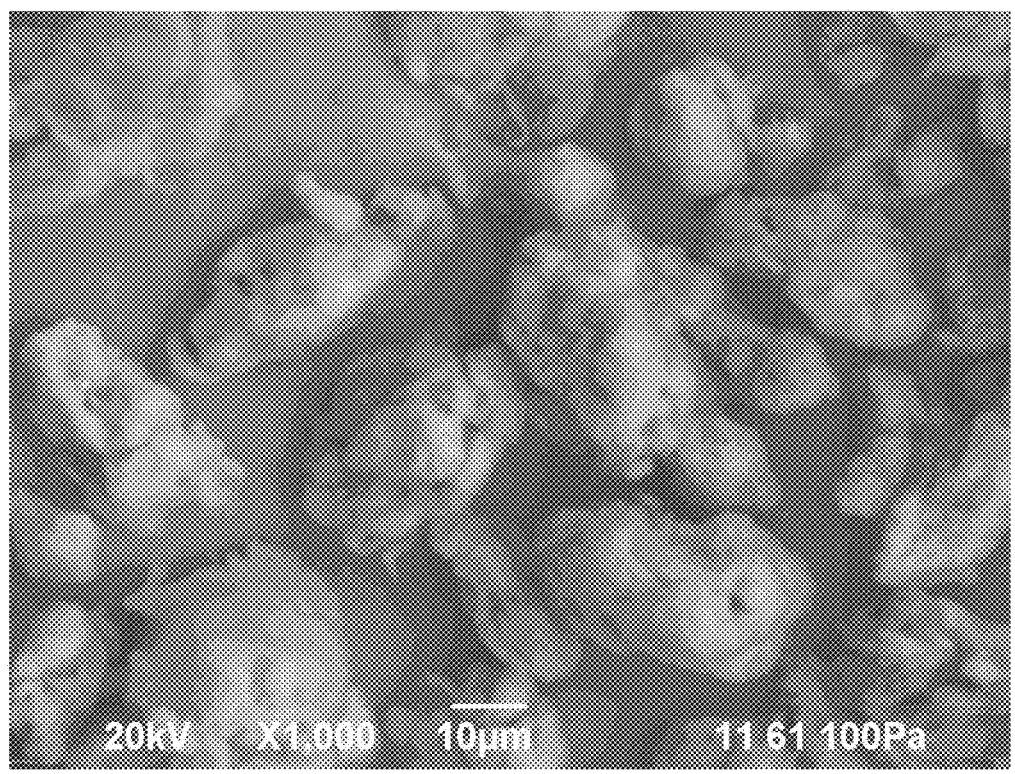
FIG. 6 is a scanning electron microscopic image of the collagen powder for which the particle size distribution was measured in Example 1.

(6) For the collagen powder prepared in the above (5), the particle size distribution was measured by a laser diffraction-scattering method. For this measurement, an apparatus manufactured by Seishin Enterprise Co., Ltd. (trade name "LMS-2000e") was employed. The average particle size, the particle size distribution and the scanning electron microscopic image of this collagen powder are shown in Table 3, FIG. 5 and FIG. 6, respectively.

(7) To 1 ml of each of the standard solutions having the respective compositions shown in Table 4 (solution A, solution B, solution C and solution D), 5 mg of the thus obtained collagen powder was added and the solubility thereof was evaluated.

(8) Further, the initial dissolution rate was measured using the solution B. Since collagens are highly hydrophilic and the difference between dissolution and swelling is not clear, the initial dissolution rate was measured as follows.

Measurement of Initial Dissolution Rate

To a cylindrical tube having an inner diameter of 10 mm, a length of 40 mm and a volume of 2 ml, a mixture of 5 mg of a sample and 1 ml of the solution B shown in Table 1 was added. The tube was tightly sealed and inversion mixing was performed at a rate of 20 inversions/minute at 180°. Here, the preparation of the solution B and the operations were performed at a temperature of 20° C. A portion of the resulting mixture was sampled 2 minutes, 4 minutes, 6 minutes, 8 minutes, 10 minutes, 15 minutes, 20 minutes and 30 minutes after the mixing. The thus sampled mixtures were each centrifuged at 5,000 rpm to obtain a supernatant, which was then subjected to SDS-polyacrylamide gel electrophoresis. The gel was stained with CBB. After destaining, the band density of the collagen was quantified using an image analysis software (NIH image) to calculate the collagen concentration in the respective supernatants. Then, based on the relationship between the elapsed time and the collagen concentration, the initial dissolution rate was calculated. It is noted here that the initial dissolution rate was calculated for the time period between the end of the mixing and not more than 10 minutes after the end of the mixing where the change in the collagen concentration exhibited linearity.

Table 5 shows the results on the solubility and Table 6 shows the results on the initial dissolution rate. Here, in Table 5, ● represents a case where the collagen powder was dissolved in less than 45 minutes; ○ represents a case where the collagen powder was dissolved in not less than 45 minutes and less than 90 minutes; Δ represents a case where the collagen powder was dissolved in not less than 90 minutes and less than 180 minutes; and x represents a case where the collagen powder was not dissolved within 180 minutes.

Figure 12:
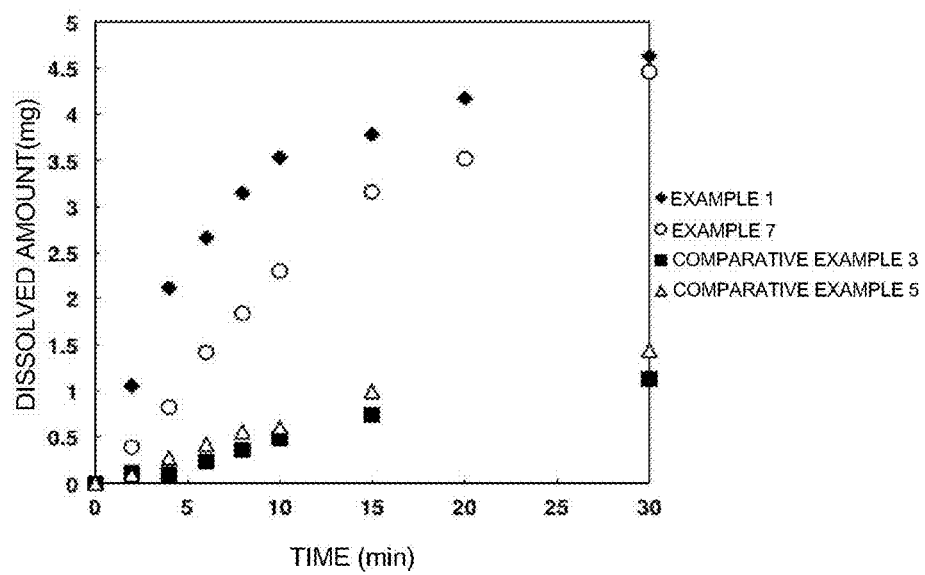
FIG. 12 is a graph based on which the initial dissolution rates of the powder collagens prepared in Examples 1 and 7 and collagen prepared in Comparative Examples 3 and 5 were calculated.

Further, FIG. 12 shows the time-course analysis of the collagen concentration of the above-described supernatants in the measurement of initial dissolution rate.

Example 2

A collagen powder was obtained in the same manner as in Example 1, except that the hydrophilic organic solvent in which the crude collagen precipitate was dispersed was changed to acetone. Using 5 mg of the thus obtained collagen powder, the solubility thereof was evaluated in the same manner as in Example 1. Table 1 shows the summary of Example 2, and the results on the solubility and initial dissolution rate are shown in Tables 5 and 6, respectively. By the addition of the respective solutions, the collagen powder was readily dissolved to form a transparent collagen solution.

Example 3

A collagen powder was obtained in the same manner as in Example 1, except that the hydrophilic organic solvent in which the crude collagen precipitate was dispersed was changed to diethyl ether. Using 5 mg of the thus obtained collagen powder, the solubility thereof was evaluated in the same manner as in Example 1. Table 1 shows the summary of Example 3, and the results on the solubility and initial dissolution rate are shown in Tables 5 and 6, respectively. By the addition of the respective solutions, the collagen powder was readily dissolved to form a transparent collagen solution.

Example 4

(1) Insoluble collagen fiber, which was obtained by grinding the dermis layer of a bovine skin using a meat grinder or the like, followed by defatting and sufficient washing, was used as a starting material. After suspending the insoluble collagen in distilled water to a collagen final concentration of 2% by mass, hydrochloric acid was added to the resulting suspension to adjust the pH to 3.0. Then, an acidic protease was added in an amount of one-hundredth of the collagen weight, and the resultant was subjected to a solubilization treatment at 25° C. for 72 hours. After terminating the enzyme reaction, to the thus obtained enzyme-solubilized collagen solution, sodium chloride was added to a final concentration of 5% by mass to perform salt precipitation, and the resulting precipitates were recovered by centrifugation. The thus recovered salt precipitates were dispersed in distilled water to a collagen concentration of 1% by mass and then uniformly dissolved by adjusting the pH of the resulting dispersion to 3.0 with an addition of hydrochloric acid. Then, after filtering the thus obtained solution through a piece of cloth and a filter paper, the filtered solution was adjusted with sodium hydroxide to have a pH of 9.0 and collagen was isoelectrically precipitated while stirring the solution using a masscolloider at a flow rate of 500 ml/min, a rotation speed of 1,500 rpm and a clearance of 50 μm. The collagen precipitates contained in the thus obtained precipitates had an average particle size of 131 μm. Subsequently, the solution was centrifuged at 17,500 rpm for 20 minutes to recover precipitates and then washed again for desalting with distilled water adjusted to have a pH of 9.0. The resulting solution was subjected to 10 rounds of the above-described centrifugation and precipitates were recovered as crude collagen precipitate. This crude collagen precipitate had a collagen concentration of 23% by mass.

Then, 50 g of the thus obtained crude collagen precipitate was added to 950 g of ethanol with a temperature of 20° C. and dispersed for 30 minutes using a homogenizer. The resulting dispersion was filtered to recover solid collagen, which was then air-dried at room temperature to obtain a collagen powder.

Figure 7:
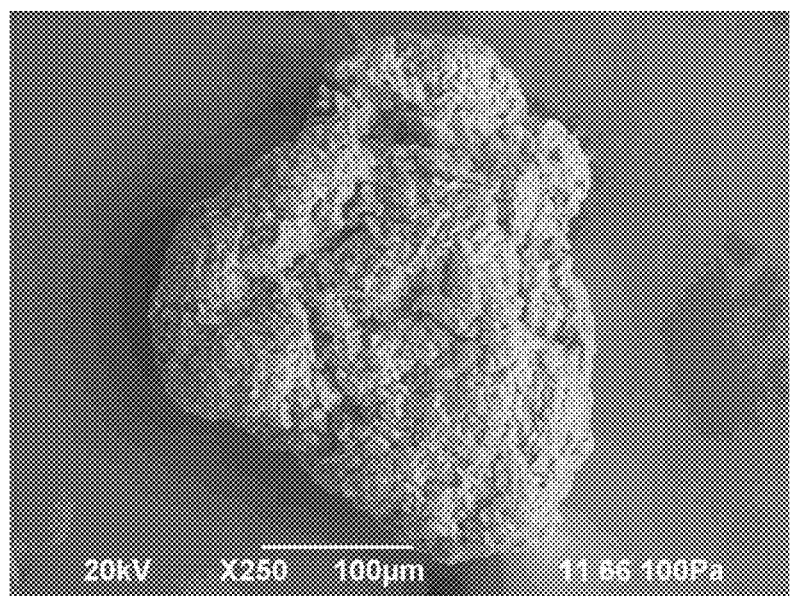
FIG. 7 is a scanning electron microscopic image of the collagen powder prepared in Example 4.

(2) The thus obtained collagen powder was observed under a scanning electron microscopic image. The result of the observation is shown in FIG. 7. It was found that the collagen powder was uneven and porous, and had an average particle size of 333 μm (3) The denaturation temperature of the thus obtained collagen powder was measured by a differential scanning calorimeter (DSC). The results are shown in Table 2. The powder collagen was observed to have a peak of large caloric change at 113° C.

Figure 8:
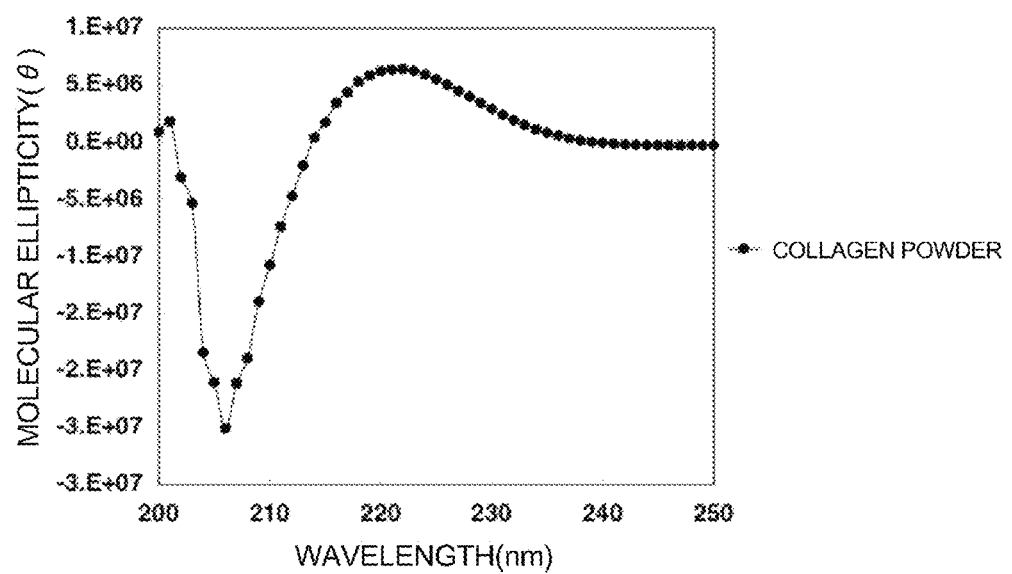
FIG. 8 is a graph showing the circular dichroism of the collagen solution in which the powder collagen prepared in Example 4 was redissolved.

(4) Then, 5 mg of the thus obtained collagen powder was redissolved in 1 ml of 10 mM acetic acid and the resultant was adjusted with 5 mM acetic acid to prepare a collagen solution having a final concentration of 0.1 mg/ml. The circular dichroism (CD) of the thus obtained collagen solution was measured at 20° C. The results are shown in FIG. 8. The redissolved collagen solution (the collagen powder of the present invention) was observed to have a peak at 221 nm, which is unique to a triple-helix structure; therefore, it was found that the redissolved collagen solution retained a triple-helix structure at 20° C.

(5) Using 5 mg of the thus obtained collagen powder, the solubility thereof was evaluated in the same manner as in Example 1. Table 1 shows the summary of Example 4, and the results on the solubility and initial dissolution rate are shown in Tables 5 and 6, respectively.

Example 5

To the enzyme-solubilized collagen solution obtained in Example 4, sodium chloride was added to a final concentration of 5% by mass, and collagen was salt-precipitated with stirring using a masscolloider at a flow rate of 500 ml/min, a rotation speed of 1,500 rpm and a clearance of 50 μm. The resulting solution was centrifuged at 17,500 rpm for 20 minutes to recover precipitates and further subjected to 10 rounds of the above-described centrifugation, thereby obtaining a crude collagen precipitate. The collagen precipitates contained in the thus obtained precipitates had an average particle size of 142 μm. This crude collagen precipitate had a collagen concentration of 38% by mass.

Then, 50 g of the thus obtained crude collagen precipitate was added to 950 g of ethanol with a temperature of 20° C.

and dispersed for 30 minutes using a homogenizer. The resulting dispersion was filtered to recover solid collagen, which was then air-dried at room temperature to obtain a collagen powder. The properties, isoelectric point, success or failure of powderization and the like of the crude collagen precipitate are shown in Table 1.

Example 6

To the enzyme-solubilized collagen solution obtained in Example 4, disodium adenosine triphosphate (ATP 2Na) was added with stirring to a final concentration of 0.22% by mass. The resultant was kept to stand on ice for one hour and then centrifuged to recover SLS collagen that were generated. The collagen precipitates contained in the thus obtained precipitates had an average particle size of 13.4 μm. The thus obtained crude collagen precipitate had a collagen concentration of 12% by mass.

Then, 80 mg of the thus obtained crude collagen precipitate was added to 20 g of ethanol with a temperature of 20° C. and dispersed for 30 minutes using a homogenizer. The resulting dispersion was filtered to recover solid collagen, which was then air-dried at room temperature to obtain a collagen powder. The properties, isoelectric point, success or failure of powderization and the like of the crude collagen precipitate are shown in Table 1.

Example 7

The alkali-solubilized collagen solution obtained in Example 1 was adjusted to have a pH of 4.5 with an addition of sodium hydroxide and the resultant was kept on ice to stand to allow collagen to be isoelectrically precipitated. Then, the resulting isoelectric precipitates were pulverized once using a masscolloider at a flow rate of 500 ml/min, a rotation speed of 1,500 rpm and a clearance of 50 μm. The collagen precipitates contained in the thus obtained precipitates had an average particle size of 724 μm. Then, after recovering precipitates by centrifugation, the resulting solution was again washed for desalting with distilled water adjusted to have a pH of 4.5. The solution was further subjected to 10 rounds of the above-described centrifugation and precipitates were recovered as crude collagen precipitate. This crude collagen precipitate had a collagen concentration of 27% by mass.

Then, 50 g of the thus obtained crude collagen precipitate was added to 950 g of ethanol with a temperature of 20° C. and dispersed for 30 minutes using a homogenizer. The resulting dispersion was filtered to recover solid collagen, which was then air-dried at room temperature to obtain a collagen powder.

Further, using 5 mg of the thus obtained collagen powder, the solubility thereof was evaluated in the same manner as in Example 1. Table 1 shows the properties, isoelectric point, success or failure of powderization and the like of the crude collagen precipitate, and the results on the solubility and initial dissolution rate are shown in Tables 5 and 6, respectively. In addition, FIG. 12 shows the time-course analysis of the collagen concentration of the above-described supernatants in the measurement of initial dissolution rate.

Example 8

The alkali-solubilized collagen solution obtained in Example 1 was adjusted to have a pH of 4.5 with an addition of sodium hydroxide and the resultant was kept on ice to stand to allow collagen to be isoelectrically precipitated. Then, the resulting isoelectric precipitates were pulverized three times using a masscolloider at a flow rate of 500 ml/min, a rotation speed of 1,500 rpm and a clearance of 50 μm. The collagen precipitates contained in the thus obtained precipitates had an average particle size of 335 μm. Then, after recovering precipitates by centrifugation, the resulting solution was again washed for desalting with distilled water adjusted to have a pH of 4.5. The solution was further subjected to 10 rounds of the above-described centrifugation and precipitates were recovered as crude collagen precipitate. This crude collagen precipitate had a collagen concentration of 28% by mass.

Then, 50 g of the thus obtained crude collagen precipitate was added to 950 g of ethanol with a temperature of 20° C. and dispersed for 30 minutes using a homogenizer. The resulting dispersion was filtered to recover solid collagen, which was then air-dried at room temperature to obtain a collagen powder.

Further, using 5 mg of the thus obtained collagen powder, the solubility thereof was evaluated in the same manner as in Example 1. Table 1 shows the properties, isoelectric point, success or failure of powderization and the like of the crude collagen precipitate, and the results on the solubility and initial dissolution rate are shown in Tables 5 and 6, respectively.

Example 9

The isoelectric precipitate of the alkali-solubilized collagen obtained in Example 1 (isoelectric point: pH 4.5) was dispersed in methanol and hydrochloric acid was added to the resulting dispersion to a final concentration of 0.1 M. The resulting solution was stirred at room temperature for 3 hours to perform esterification reaction. Then, by adjusting the solution to have neutral pH with sodium hydroxide solution, the reaction was terminated and collagen was allowed to precipitate. After recovering precipitates by centrifugation, the thus recovered precipitates were redissolved in 10 mM acetic acid to obtain methyl-esterified collagen. The thus obtained methyl-esterified collagen had an isoelectric point at pH 7.9.

Thereafter, to the thus obtained methyl-esterified collagen solution, sodium chloride was added to a final concentration of 5% by mass, and the resulting solution was salt-precipitated while stirring the solution with a homogenizer. Subsequently, the solution was centrifuged at 17,500 rpm for 20 minutes to recover precipitates and further subjected to 10 rounds of the above-described centrifugation, thereby obtaining crude collagen precipitate. The collagen precipitates contained in the thus obtained precipitate had an average particle size of 244 μm and the collagen concentration was 29% by mass.

Then, 0.5 g of the thus obtained crude collagen precipitate was added to 9.5 g of ethanol with a temperature of 20° C. and dispersed for 30 minutes using a homogenizer. The resulting dispersion was filtered to recover solid collagen, which was then air-dried at room temperature to obtain a collagen powder. Table 1 shows the properties, isoelectric point, success or failure of powderization and the like of the crude collagen precipitate.

Example 10

The enzyme-solubilized collagen solution obtained in Example 4 (isoelectric point: pH 9.0) was adjusted to have a pH of 8 to 9 with an addition of sodium hydroxide solution, thereby collagen was isoelectrically precipitated. To the thus obtained isoelectric precipitate dispersion, succinic anhydride was added to a final concentration of 0.5 mM, and the resulting solution was stirred at room temperature for 1 hour to perform acylation reaction. After the reaction, by making the solution acidic with an addition of hydrochloric acid and then further adding sodium chloride to a final concentration of 5% by mass, the reaction was terminated and succinylated collagen was allowed to precipitate. After recovering precipitates by centrifugation, the thus obtained succinylated collagen was redissolved in 10 mM acetic acid to obtain succinylated collagen. The thus obtained succinylated collagen had an isoelectric point of 5.4.

Thereafter, to the thus obtained succinylated collagen solution, sodium chloride was added to a final concentration of 5% by mass, and the resulting solution was salt-precipitated while stirring the solution with a homogenizer. Subsequently, the solution was centrifuged at 17,500 rpm for 20 minutes to recover precipitates and further subjected to 10 rounds of the above-described centrifugation, thereby obtaining crude collagen precipitate. The collagen precipitates contained in the thus obtained precipitate had an average particle size of 167 μm and the collagen concentration was 42% by mass.

Then, 0.5 g of the thus obtained crude collagen precipitate was added to 9.5 g of ethanol with a temperature of 20° C. and dispersed for 30 minutes using a homogenizer. The resulting dispersion was filtered to recover solid collagen, which was then air-dried at room temperature to obtain a collagen powder. Table 1 shows the properties, isoelectric point, success or failure of powderization and the like of the crude collagen precipitate.

Example 11

To the enzyme-solubilized collagen solution obtained in Example 4 (isoelectric point: 9.0), 5 times concentration of PBS(−) was added to adjust the collagen concentration to be 0.75 mg/ml. The resulting solution was stirred at 37° C. overnight to allow reconstituted fibrils to be formed. The resulting reconstituted fibrils dispersion was pulverized by a homogenizer to prepare a dispersion of fine reconstituted fibrils. The thus obtained regenerated fiber dispersion was centrifuged at 17,500 rpm for 20 minutes to recover precipitates and further subjected to 10 rounds of the above-described centrifugation, thereby obtaining crude collagen precipitate. The collagen precipitates contained in the thus obtained precipitate had an average particle size of 213 μm and this crude collagen precipitate had a collagen concentration of 30% by mass.

Then, 0.5 g of the thus obtained crude collagen precipitate was added to 9.5 g of ethanol with a temperature of 20° C. and dispersed for 30 minutes using a homogenizer. The resulting dispersion was filtered to recover solid collagen, which was then air-dried at room temperature to obtain a collagen powder. Table 1 shows the properties, isoelectric point, success or failure of powderization and the like of the crude collagen precipitate.

Comparative Example 1

To 950 g of ethanol with a temperature of 20° C., 50 g of the alkali-solubilized collagen solution obtained in Example 1 (final concentration of 1% by mass) was added and dispersed for 30 minutes using a homogenizer. The resulting dispersion was then filtered. However, the dispersed collagen that was filtered was obtained in the form of a film, not in the form of powder. Table 1 shows the properties, isoelectric point, success or failure of powderization and the like of the crude collagen precipitate.

Comparative Example 2

The alkali-solubilized collagen solution obtained in Example 1 was adjusted to have a pH of 4.5 with an addition of sodium hydroxide and collagen was isoelectrically precipitated while stirring the solution using a masscolloider at a flow rate of 500 ml/min, a rotation speed of 1,500 rpm and a clearance of 50 μm. The collagen precipitates contained in the thus obtained precipitates had an average particle size of 141 μm. Then, after recovering precipitates by subjecting the solution to 20-minute centrifugation at 17,500 rpm, the resulting solution was again washed for desalting with distilled water adjusted to have a pH of 4.5, thereby recovering precipitates as crude collagen precipitate. This crude collagen precipitate had a collagen concentration of 10% by mass.

Then, 50 g of the thus obtained crude collagen precipitate was added to 950 g of ethanol with a temperature of 20° C. and dispersed for 30 minutes using a homogenizer, and the resulting dispersion was filtered. However, the dispersed collagen that was filtered was obtained in the form of a film, not in the form of powder. Table 1 shows the properties, isoelectric point, success or failure of powderization and the like of the crude collagen precipitate.

Comparative Example 3

Figure 9:
FIG. 9 is a phase contrast microscopic image of the collagen precipitate prepared in Comparative Example 3.

(1) The alkali-solubilized collagen solution obtained in Example 1 was adjusted to have a pH of 4.5 with an addition of sodium hydroxide and the resultant was kept on ice to stand to allow collagen to be isoelectrically precipitated. The collagen precipitates contained in the thus obtained precipitates had an average particle size of 1,858 μm. Then, after recovering precipitates by centrifugation, the resulting solution was again washed for desalting with distilled water adjusted to have a pH of 4.5. The solution was further subjected to 10 rounds of the above-described centrifugation and precipitates were recovered as crude collagen precipitate. This crude collagen precipitate had a collagen concentration of 33% by mass. FIG. 9 shows a phase contrast microscopic image of the thus obtained collagen precipitate.

Then, 50 g of the thus obtained crude collagen precipitate was added to 950 g of ethanol with a temperature of 20° C. and dispersed for 30 minutes using a homogenizer, and the resulting dispersion was filtered. However, the dispersed collagen that was filtered was obtained in the form of a film, not in the form of powder.

(2) Using 5 mg of the thus obtained collagen solid, the solubility thereof was evaluated in the same manner as in Example 1. Table 1 shows the summary of Comparative Example 3, and the results on the solubility and initial dissolution rate are shown in Tables 5 and 6, respectively. In addition, FIG. 12 shows the time-course analysis of the collagen concentration of the above-described supernatants in the measurement of initial dissolution rate.

Comparative Example 4

(1) The isoelectric precipitate of the alkali-solubilized collagen obtained in Example 1 was dispersed in distilled water such that the final concentration became 3% and the resultant was homogenized for 30 minutes to obtain a uniform dispersion. Using a spray dryer whose hot air temperature was adjusted to be 120° C. at the inlet and 60°

C. at the outlet, the thus obtained dispersion was spray-dried to obtain a collagen powder. Table 1 shows the summary of Comparative Example 4 and Table 4 shows the results on the solubility.

The collagen powder obtained by the spray-drying was dissolved only about 20% even after 20 hours. Since the starting material of the collagen precipitate was the same as the one used in Example 1, the difference in the solubility between this collagen powder and the one obtained in Example 1 is not attributable to the difference in the collagen molecules, but to the difference in the shape which is dependent on the treatment process. When the undissolved collagen powder was observed, it was found that the spray-dried collagen powder was fine powder and that the collagen powder was consequently in the form of lumps and only the surfaces of the lumps were semitransparency and dissolved. In the spray-drying, the resulting collagen particles had a small average particle size of 4.60 μm and the surfaces thereof were relatively smooth, so that the solution was not likely to permeate into the lumps, and this is believed to be reason for the poor solubility. In contrast to this, none of the collagen powders of Examples 1 to 4 and 7 to 10 formed a lump.

Figure 10:
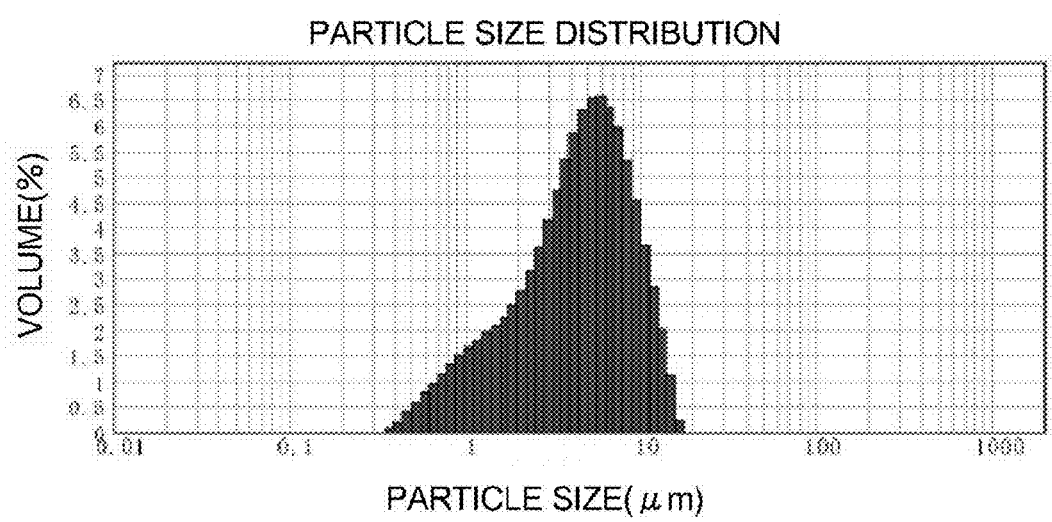
FIG. 10 is a graph showing the particle size distribution of the collagen powder obtained in Comparative Example 4.
Figure 11:
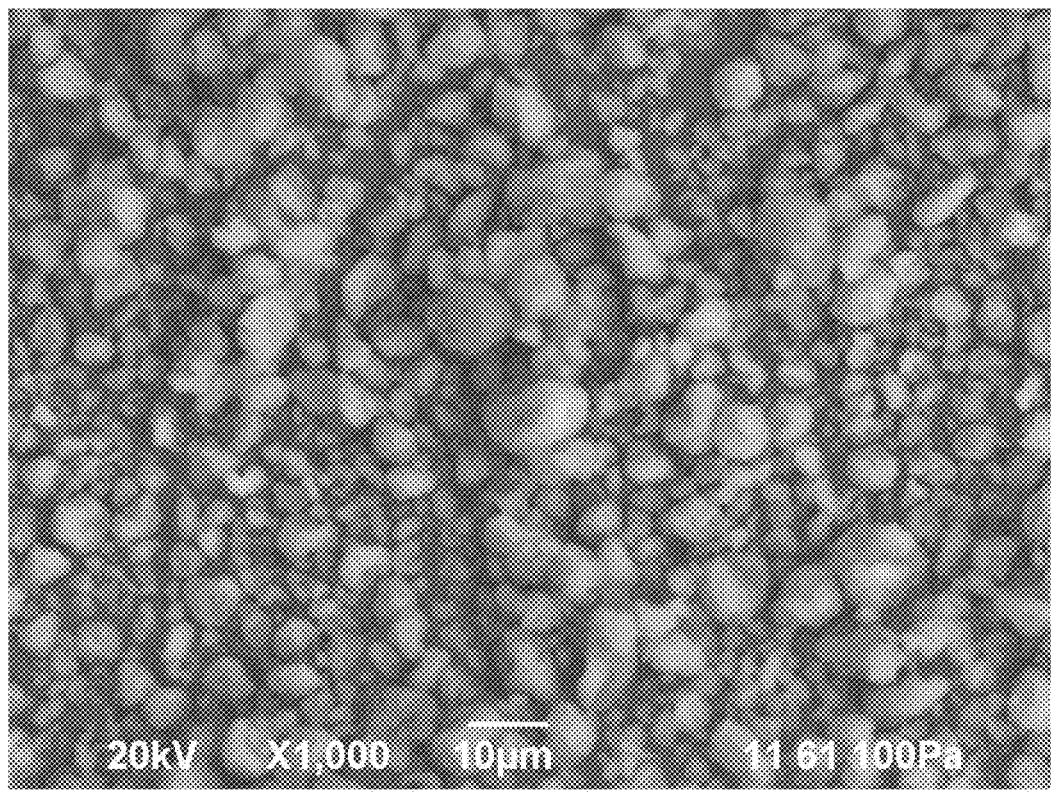
FIG. 11 is a scanning electron microscopic image of the collagen powder obtained by using a spray dryer for drying in Comparative Example 4.

(2) For the collagen powder prepared in the above (1), in the same manner as in Example 1, the specific surface area was measured by a single-point BET method and the particle size distribution was measured by a laser diffraction-scattering method. Table 3 shows the specific surface area and the average particle size. Further, FIG. 10 shows the particle size distribution and FIG. 11 shows a scanning electron microscopic image of the collagen powder.

Comparative Example 5

Figure 13:
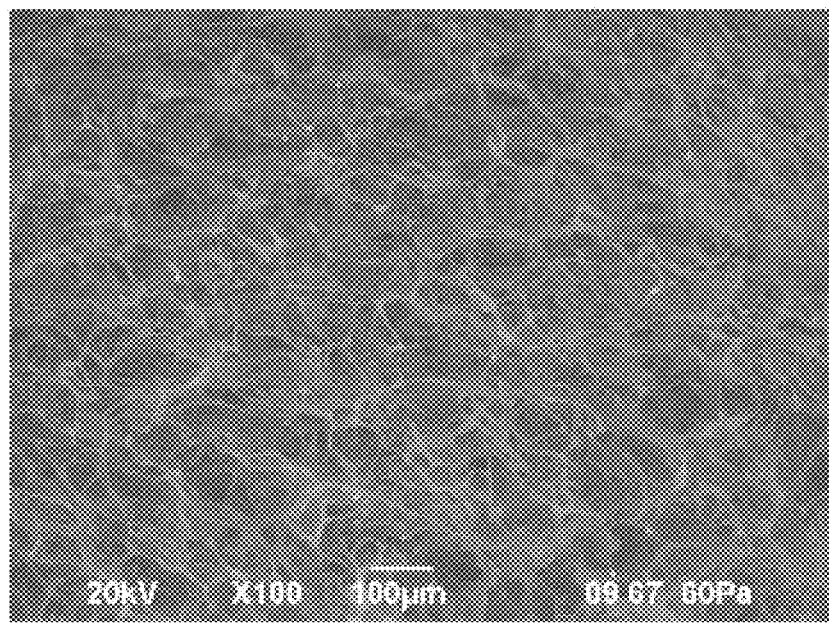
FIG. 13 is a scanning electron microscopic image of the collagen sponge obtained in Comparative Example 5.

(1) The crude collagen precipitate obtained in Example 1 was redissolved in hydrochloric acid to a final concentration of 1% by mass and the resulting solution was subsequently neutralized with sodium hydroxide to obtain an alkali-solubilized collagen solution of pH 7.5. The thus alkali-solubilized collagen solution obtained solution was then freeze-dried to prepare a collagen sponge. FIG. 13 shows a scanning electron microscopic image of the collagen sponge.

(2) Using 5 mg of the thus obtained collagen sponge, the solubility thereof was evaluated in the same manner as in Example 1. Table 1 shows the summary of Comparative Example 5, and the results on the solubility and initial dissolution rate are shown in Tables 5 and 6, respectively. Further, FIG. 12 shows the time-course analysis of the collagen concentration of the above-described supernatants in the measurement of initial dissolution rate.

Comparative Example 6

Figure 14:
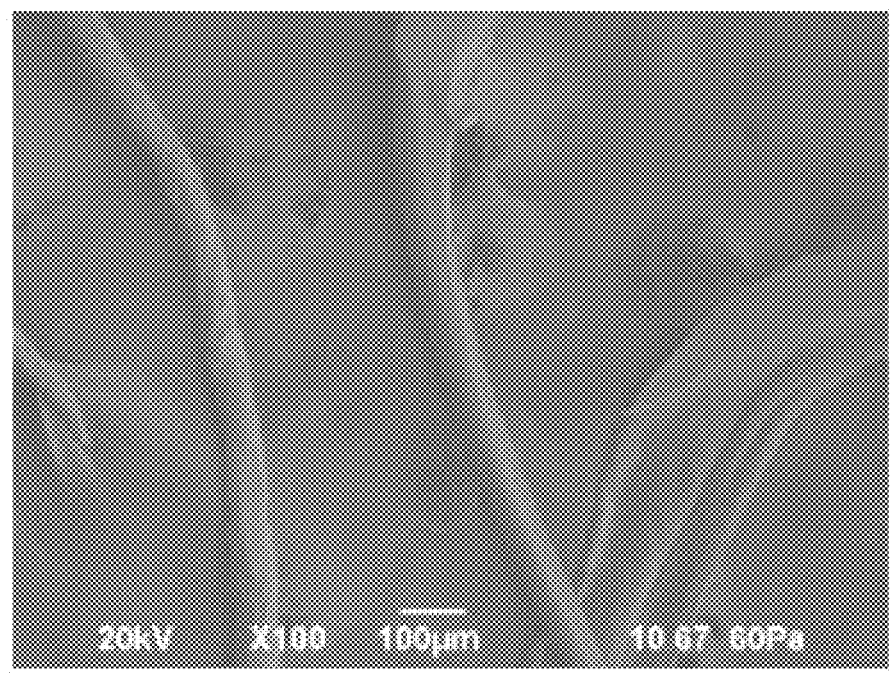
FIG. 14 is a scanning electron microscopic image of the collagen fiber obtained in Comparative Example 6.

The crude collagen precipitate obtained in Example 1 was redissolved in hydrochloric acid to a final concentration of 1% by mass and the resulting solution was subsequently neutralized with sodium hydroxide to obtain an alkali-solubilized collagen solution of pH 7.5. Using a 27-gauge injection needle, the thus obtained alkali-solubilized collagen solution was injected into ethanol and then air-dried to prepare a collagen thread. FIG. 14 shows a scanning electron microscopic image of the thus obtained collagen thread.

(2) Using 5 mg of the thus obtained collagen fiber, the solubility thereof was evaluated in the same manner as in Example 1. Table 1 shows the summary of Comparative Example 6, and the results on the solubility and initial dissolution rate are shown in Tables 5 and 6, respectively.

TABLE 1

| | | Crude collagen precipitate or the like | | | | | | Powderization | |
| --- | --- | --- | --- | --- | --- | --- | --- | --- | --- |
| | Property | Concentration (% by mass) | Isoelectric point (pH) | Average particle size (μm) | Hydrophilic organic solvent Type | Amount* | Drying | Success/Failure | Average particle size (μm) |
| Example 1 | Isoelectric precipitate | 30 | 4.5 | 141 | ethanol | 19 | air-drying vibration drying | powder powder | 158 68.1 |
| Example 2 | Isoelectric precipitate | 30 | 4.5 | 141 | acetone | 19 | air-drying | powder | 93.5 |
| Example 3 | Isoelectric precipitate | 30 | 4.5 | 141 | diethyl ether | 19 | air-drying | powder | 270 |
| Example 4 | Isoelectric precipitate | 23 | 9.0 | 131 | ethanol | 19 | air-drying | powder | 333 |
| Example 5 | Salt precipitate | 38 | 9.0 | 142 | ethanol | 19 | air-drying | powder | 326 |
| Example 6 | SLS precipitate | 12 | 9.0 | 13.4 | ethanol | 250 | air-drying | powder | 107 |
| Example 7 | Isoelectric precipitate | 27 | 4.5 | 724 | ethanol | 19 | air-drying | powder | 776 |
| Example 8 | Isoelectric precipitate | 28 | 4.5 | 335 | ethanol | 19 | air-drying | powder | 646 |
| Example 9 | Salt precipitate | 29 | 7.9 | 244 | ethanol | 19 | air-drying | powder | 391 |
| Example 10 | Salt precipitate | 42 | 5.4 | 167 | ethanol | 19 | air-drying | powder | 277 |
| Example 11 | Reconstituted fibrils | 30 | 9.0 | 213 | ethanol | 19 | air-drying | powder | 136 |
| Comparative Example 1 | Solution | 1.0 | 4.5 | — | ethanol | 19 | air-drying | film | — |
| Comparative Example 2 | Isoelectric precipitate | 10 | 4.5 | 141 | ethanol | 19 | air-drying | film | — |
| Comparative Example 3 | Isoelectric precipitate | 33 | 4.5 | 1,858 | ethanol | 19 | air-drying | film | — |

TABLE 1-continued

| | | Crude collagen precipitate or the like | | | | | Powderization | | |
|---|---|---|---|---|---|---|---|---|---|
| | | Concentration | Isoelectric point | Average particle size | Hydrophilic organic solvent | | | | Average particle size |
| | Property | (% by mass) | (pH) | (μm) | Type | Amount* | Drying | Success/Failure | (μm) |
| Comparative Example 4 | Isoelectric precipitate | 30 | 4.5 | 141 | — | — | spray-drying | powder | 4.60 |
| Comparative Example 5 | Solution | 1.0 | 4.5 | — | — | — | freeze-drying | sponge | — |
| Comparative Example 6 | Solution | 1.0 | 4.5 | — | — | — | air-drying | thread | — |

*Mass times with respect to the crude precipitate

TABLE 2

| | Example 1 | | Example 4 | |
|---|---|---|---|---|
| | Solution | Powder | Solution | Powder |
| Thermal denaturation onset temperature (° C.) | 28.6 | 102.5 | 27.6 | 90.4 |
| Thermal denaturation peak temperature (° C.) | 33.0 | 112.4 | 38.1 | 113.9 |
| Thermal denaturation end temperature (° C.) | 36.4 | 116.1 | 43.3 | 118.9 |

TABLE 3

| | Sample weight (g) | Specific surface area (m²/g) | Average particle size (μm) |
|---|---|---|---|
| Example 1 | 1.60390 | 1.6521 | 68.1 |
| Comparative Example 4 | 1.97692 | 1.49240 | 4.60 |

TABLE 4

| Component | Solution A | Solution B | Solution C | Solution D |
|---|---|---|---|---|
| Sodium citrate | 1.0% | 1.0% | 1.0% | 1.0% |
| Citric acid | 0.2% | 0.04% | 0.004% | 0.0% |
| Distilled water | 98.8% | 98.96% | 98.996% | 99.0% |
| pH | 5.5 | 6.5 | 7.5 | 8.2 |

Unit: % by mass

TABLE 5

| | Solution A (pH 5.5) | Solution B (pH 6.5) | Solution C (pH 7.5) | Solution D (pH 8.2) |
|---|---|---|---|---|
| Example 1 | ● | ● | ● | ● |
| Example 2 | ● | ● | ● | ● |
| Example 3 | ● | ● | ● | ● |
| Example 7 | ○ | ○ | ○ | ○ |
| Example 8 | ○ | ○ | ○ | ○ |
| Example 9 | ● | ● | ● | ● |
| Example 10 | ● | ● | ● | ● |
| Example 4 | X | X | X | X |
| Comparative Example 3 | X | X | X | X |
| Comparative Example 4 | X | X | X | X |
| Comparative Example 5 | Δ | Δ | Δ | Δ |
| Comparative Example 6 | Δ | Δ | Δ | Δ |

TABLE 6

| | Initial dissolution rate (mg/min) |
|---|---|
| Example 1 | 0.53 |
| Example 2 | 0.53 |
| Example 3 | 0.53 |
| Example 7 | 0.24 |
| Example 8 | 0.22 |
| Example 9 | 0.51 |
| Example 10 | 1.01 |
| Example 4 | 0.0 |
| Comparative Example 3 | 0.05 |
| Comparative Example 5 | 0.07 |
| Comparative Example 6 | 0.04 |

The present invention is based on Japanese Patent Application Nos. 2010-172698 and 2010-172699, which were filed on Jul. 30, 2010. The specifications, claims and drawings of Japanese Patent Application Nos. 2010-172698 and 2010-172699 are hereby incorporated by reference in their entirety.

INDUSTRIAL APPLICABILITY

According to the present invention, a fine collagen powder and/or a fine collagen derivative powder can be produced with simple operations. Furthermore, the resulting collagen powder and the like have excellent thermal stability and are capable of forming a triple-helix structure in a solution; therefore, the collagen powder and the like are useful.

The invention claimed is:

1. A collagen powder and/or a collagen derivative powder, which are obtained by
dispersing in a hydrophilic organic solvent a crude collagen precipitate which comprises 12 to 50% by mass of a collagen precipitate and/or a collagen derivative precipitate having an average particle size of 1 to 1,000 μm, prepared by salt precipitation or isoelectric precipitation of solubilized collagen and/or solubilized collagen derivative,
recovering solids and
then drying the solids to obtain the collagen powder and/or the collagen derivative powder,
wherein the collagen powder and/or collagen derivative powder have an initial dissolution rate of not less than 0.2 mg/min. in a pH 6.5 solution comprising 5 mg of the collagen powder and/or the collagen derivative powder.

2. The collagen powder and/or the collagen derivative powder according to claim 1, wherein the crude collagen precipitate is an isoelectric precipitate of solubilized collagen and/or solubilized collagen derivative obtained at a pH of 3.5 to 10 or a salt precipitate.

3. The collagen powder and/or the collagen derivative powder according to claim 1, wherein:
the crude collagen precipitate has an isoelectric point at a pH of 3.5 to 8.0.

4. A method of producing a collagen powder and/or a collagen derivative powder, comprising the steps of:
obtaining isoelectric precipitates having an average particle size of 1 to 1,000 μm by isoelectrically precipitating a solution containing solubilized collagen and/or solubilized collagen derivative at a pH of 3.5 to 10 while controlling association of the collagen and/or the collagen derivative;
adjusting the concentration of the resulting collagen precipitate and/or collagen derivative precipitate in the range of 12 to 50% by mass, comprising centrifugation and/or filtration of the precipitate, thereby preparing a crude collagen precipitate;
dispersing the thus obtained crude collagen precipitate in a hydrophilic organic solvent;
recovering solids; and
drying the solids to obtain the collagen powder and/or the collagen derivative powder,
wherein the collagen powder and/or collagen derivative powder have an initial dissolution rate of not less than 0.2 mg/min. in a pH 6.5 solution comprising 5 mg of the collagen powder and/or the collagen derivative powder.

5. The method according to claim 4, wherein the association of the collagen is controlled by stirring the solution containing the collagen and/or the collagen derivative.

6. A method of producing a collagen powder and/or a collagen derivative powder, comprising the steps of:
obtaining isoelectric precipitates having an average particle size of 1 to 1,000 μm by isoelectrically precipitating a solution containing solubilized collagen and/or solubilized collagen derivative at a pH of 3.5 to 10 and then pulverizing the resulting precipitates;
adjusting the concentration of the resulting collagen precipitate and/or collagen derivative precipitate in the range of 12 to 50% by mass, comprising centrifugation and/or filtration of the precipitate, thereby preparing a crude collagen precipitate;
dispersing the thus obtained crude collagen precipitate in a hydrophilic organic solvent;
recovering solids; and
drying the solids to obtain the collagen powder and/or the collagen derivative powder,
wherein the collagen powder and/or collagen derivative powder have an initial dissolution rate of not less than 0.2 mg/min. in a pH 6.5 solution comprising 5 mg of the collagen powder and/or the collagen derivative powder.

7. A method of producing a collagen powder and/or a collagen derivative powder, comprising the steps of:
obtaining salt precipitates having an average particle size of 1 to 1,000 μm by subjecting a solution containing solubilized collagen and/or solubilized collagen derivative to salt precipitation while controlling association of the collagen and/or the collagen derivative;
adjusting the concentration of the resulting collagen precipitate and/or collagen derivative precipitate contained in the salt precipitates in the range of 12 to 50% by mass, comprising centrifugation and/or filtration of the precipitate, thereby preparing a crude collagen precipitate;
dispersing the thus obtained crude collagen precipitate in a hydrophilic organic solvent;
recovering solids; and
drying the solids to obtain the collagen powder and/or the collagen derivative powder,
wherein the collagen powder and/or collagen derivative powder have an initial dissolution rate of not less than 0.2 mg/min. in a pH 6.5 solution comprising 5 mg of the collagen powder and/or the collagen derivative powder.

8. A method of producing a collagen powder and/or a collagen derivative powder, comprising the steps of:
obtaining salt precipitates having an average particle size of 1 to 1,000 μm by subjecting a solution containing solubilized collagen and/or solubilized collagen derivative to salt precipitation and then pulverizing the resulting salt precipitates;
adjusting the concentration of the resulting collagen precipitate and/or collagen derivative precipitate contained in the salt precipitates in the range of 12 to 50% by mass, comprising centrifugation and/or filtration of the precipitate, thereby preparing a crude collagen precipitate;
dispersing the thus obtained crude collagen precipitate in a hydrophilic organic solvent;
recovering solids; and
drying the solids to obtain the collagen powder and/or the collagen derivative powder,
wherein the collagen powder and/or collagen derivative powder have an initial dissolution rate of not less than 0.2 mg/min. in a pH 6.5 solution comprising 5 mg of the collagen powder and/or the collagen derivative powder.

9. The method according to any one of claims 4 to 8, wherein the hydrophilic organic solvent comprises an alcohol, a ketone, an ether or a mixture thereof.

10. The collagen derivative powder of claim 1 comprising acylated and/or esterified collagen.

11. The collagen derivative powder of claim 10, which comprises succinylated collagen, phthalated collagen or maleylated collagen.

12. The collagen derivative powder of claim 10, which comprises collagen esterified with a monohydric alcohol.

13. The collagen derivative powder of claim 10, which comprises collagen esterified with a polyhydric alcohol.

14. A collagen powder and/or a collagen derivative powder, which powder comprises 12 to 50% by mass of a collagen precipitate and/or a collagen derivative precipitate having an average particle size of 1 to 1,000 μm,
wherein the collagen precipitate and/or the collagen derivative precipitate is precipitate of solubilized collagen and/or solubilized collagen derivative,
wherein the collagen powder and/or collagen derivative powder have an initial dissolution rate of not less than 0.2 mg/min. in a pH 6.5 solution comprising 5 mg of the collagen powder and/or the collagen derivative powder.

15. A collagen powder and/or a collagen derivative powder of new claim 14, wherein the powder is porous.

16. A collagen powder and/or a collagen derivative powder of claim 14 or 15, wherein the powder has an average particle size of 8 to 1,000 μm and an specific surface area of 0.8 to 30 $m^2/g$.

17. A collagen powder and/or a collagen derivative powder of claim 14 or 15, wherein the powder has an average particle size of 8 to 1,000 μm and an initial dissolution rate of not less than 0.2 mg/min in a pH 6.5 solution.

18. A collagen powder and/or a collagen derivative powder of claim 14 or 15, wherein the collagen precipitate and/or the collagen derivative precipitate comprises the solubilized collagen and or the solubilized collagen derivative in a triple-helix structure.

19. A collagen powder, which is obtained by a method comprising the steps of:

dispersing in a hydrophilic organic solvent a crude collagen precipitate which comprises 12 to 50% by mass of a collagen precipitate having an average particle size of 1 to 1,000 μm, prepared by salt precipitation or isoelectric precipitation of solubilized collagen, recovering solids and drying the solids to obtain the collagen powder, wherein the collagen precipitate consists essentially of salts and enzymatically treated collagen fiber isolated from an animal.

20. The collagen powder of claim 19, which is obtained by a method consisting essentially of the steps in claim 19.

21. The collagen powder of claim 19, which is obtained by a method consisting of the steps in claim 20.

22. A method of producing a collagen powder, consisting essentially the steps of:

obtaining solubilized collagen by solubilization treatment, obtaining isoelectric precipitates having an average particle size of 1 to 1,000 μm by isoelectrically precipitating a solution containing solubilized collagen at a pH of 3.5 to 10 while controlling association of the collagen;

adjusting the concentration of the resulting collagen precipitate in the range of 12 to 50% by mass comprising centrifugation and/or filtration of the precipitate, thereby preparing a crude collagen precipitate;

dispersing the thus obtained crude collagen precipitate in a hydrophilic organic solvent;

recovering solids; and drying the solids to obtain the collagen powder.

23. The method of producing the collage powder of claim 22, consisting of the steps in claim 22.

24. A method of producing a collagen powder, consisting essentially the steps of:

obtaining solubilized collagen by solubilization treatment, obtaining isoelectric precipitates having an average particle size of 1 to 1,000 μm by isoelectrically precipitating a solution containing solubilized collagen at a pH of 3.5 to 10 and then pulverizing the resulting precipitates;

adjusting the concentration of the resulting collagen precipitate in the range of 12 to 50% by mass comprising centrifugation and/or filtration of the precipitate, thereby preparing a crude collagen precipitate;

dispersing the thus obtained crude collagen precipitate in a hydrophilic organic solvent;

recovering solids; and drying the solids to obtain the collagen powder.

25. The method of producing the collagen powder of claim 24, consisting of the steps in claim 24.

* * * * *